United States Patent
Romero Amandi De Sousa et al.

(10) Patent No.: US 11,352,447 B2
(45) Date of Patent: Jun. 7, 2022

(54) GELLAN GUM HYDROGELS, PREPARATION, METHODS AND USES THEREOF

(71) Applicant: STEMMATTERS, BIOTECNOLOGIA E MEDICINA REGENERATIVA, S.A., Barco Gmr (PT)

(72) Inventors: Rui Pedro Romero Amandi De Sousa, Matosinhos (PT); Cristina Correia, São Mamede Escariz (PT); David Alexander Learmonth, Alfena (PT)

(73) Assignee: STEMMATTERS, BIOTECNOLOGIA E MEDICINA REGENERATIVA, S.A., Barco Gmr (PT)

( * ) Notice: Subject to any disclaimer, the term of this patent is extended or adjusted under 35 U.S.C. 154(b) by 858 days.

(21) Appl. No.: 16/087,699

(22) PCT Filed: Mar. 24, 2017

(86) PCT No.: PCT/IB2017/051718
§ 371 (c)(1),
(2) Date: Sep. 24, 2018

(87) PCT Pub. No.: WO2017/163222
PCT Pub. Date: Sep. 28, 2017

(65) Prior Publication Data
US 2019/0330384 A1    Oct. 31, 2019

(30) Foreign Application Priority Data
Mar. 24, 2016 (PT) .......................................... 109259

(51) Int. Cl.
| | |
|---|---|
| C08B 37/00 | (2006.01) |
| A61K 47/36 | (2006.01) |
| A61K 9/00 | (2006.01) |
| A61K 9/06 | (2006.01) |
| A61K 9/70 | (2006.01) |
| A61K 35/28 | (2015.01) |
| A61K 35/32 | (2015.01) |
| A61L 27/52 | (2006.01) |
| C12N 5/077 | (2010.01) |

(52) U.S. Cl.
CPC .......... *C08B 37/006* (2013.01); *A61K 9/0019* (2013.01); *A61K 9/06* (2013.01); *A61K 9/7023* (2013.01); *A61K 35/28* (2013.01); *A61K 35/32* (2013.01); *A61K 47/36* (2013.01); *A61L 27/52* (2013.01); *C12N 5/0655* (2013.01); *C12N 2500/30* (2013.01); *C12N 2533/70* (2013.01)

(58) Field of Classification Search
None
See application file for complete search history.

(56) References Cited

U.S. PATENT DOCUMENTS

| | | |
|---|---|---|
| 6,242,035 B1 | 6/2001 | Clark et al. |
| 8,968,716 B2 | 3/2015 | Park et al. |
| 2012/0016390 A1 | 1/2012 | Lee et al. |
| 2015/0374838 A1* | 12/2015 | Kurisawa ............... A61K 38/21 424/497 |

FOREIGN PATENT DOCUMENTS

| | | | |
|---|---|---|---|
| AU | 2011381641 A1 | 4/2014 | |
| EP | 2784101 A1 | 10/2014 | |
| IT | 1247158 B | 12/1994 | |
| WO | 2009101518 A2 | 8/2009 | |
| WO | 2011059326 A2 | 5/2011 | |
| WO | 2011119059 A1 | 9/2011 | |
| WO | 2013123946 A1 | 8/2013 | |
| WO | WO-2014167513 A1 * | 10/2014 | ............... C08K 7/14 |
| WO | 2015175655 A1 | 11/2015 | |

OTHER PUBLICATIONS

Kurisawa, Chem. Commun., 2005, 4312-4314. (Year: 2005).*
Barrett et al. "pH-Based Regulation of Hydrogel Mechanical Properties Through Mussel-Inspired Chemistry and Processing." Advanced Functional Materials 23.9 (2013): 1111-1119.
Cencer et al. "Effect of nitro-functionalization on the cross-linking and bioadhesion of biomimetic adhesive moiety." Biomacromolecules 16.1 (2014): 404-410.

(Continued)

Primary Examiner — Layla D Berry
(74) Attorney, Agent, or Firm — Leason Ellis LLP

(57) ABSTRACT

Gellan gum-based hydrogels are disclosed herein for in vitro cell culture and tissue engineering and regenerative medicine applications. Such gellan gum-based hydrogels may be used alone or combined with live cells and/or biomolecules for application in humans and/or animals. Chemical modification of gellan gum with selected ion-chelating substituents affords novel gellan gum hydrogels endowed with tunable physicochemical and biological properties. The modified gellan gum hydrogels described herein present advantages over existing hydrogel systems, including solubility, ionic crosslinking versatility, ease of formulation and injectability and greater adhesiveness within biological tissues and surfaces, whilst maintaining encapsulated cells viable during long culture periods and up-regulating the expression of healthy extracellular matrix markers.

30 Claims, 10 Drawing Sheets

(56) References Cited

OTHER PUBLICATIONS

Ding et al. "Nitro-Group Functionalization of Dopamine and its Contribution to the Viscoelastic Properties of Catechol-Containing Nanocomposite Hydrogels." Macromolecular Chemistry and Physics 216.10 (2015): 1109-1119.
Dobbin et al. "Synthesis, physicochemical properties, and biological evaluation of N-substituted 2-alkyl-3-hydroxy-4(1H)-pyridinones: orally active iron chelators with clinical potential." Journal of Medicinal Chemistry 36.17 (1993): 2448-2458.
Doner. "Rapid purification of commercial gellan gum to highly soluble and gellable monovalent cation salts." Carbohydrate polymers 32.3-4 (1997): 245-247.
Gong et al. "An improved injectable polysaccharide hydrogel: modified gellan gum for long-term cartilage regeneration in vitro." Journal of Materials Chemistry 19.14 (2009): 1968-1977.
Hamcerencu et al. "Synthesis and characterization of new unsaturated esters of Gellan Gum." Carbohydrate Polymers 71.1 (2008): 92-100.
Hashimoto et al. "Characterization of α-L-rhamnosidase of *Bacillus* sp. GL1 responsible for the complete depolymerization of gellan." Archives of Biochemistry and Biophysics 368.1 (1999): 56-60.
International Search Report in corresponding International Patent Application No. PCT/IB2017/051718, dated Jun. 23, 2017. 2 pages.

Lee et al. "Bioinspired, calcium-free alginate hydrogels with tunable physical and mechanical properties and improved biocompatibility." Biomacromolecules 14.6 (2013): 2004-2013.
McCarthy et al. "Synthesis and renal vasodilator activity of 2-chlorodopamine and N-substituted derivatives." Journal of Medicinal Chemistry 29.9 (1986): 1586-1590.
Oliveira et al. "Gellan gum injectable hydrogels for cartilage tissue engineering applications: in vitro studies and preliminary in vivo evaluation." Tissue Engineering Part A 16.1 (2009): 343-353.
Rodenstein et al. "Fabricating chemical gradients on oxide surfaces by means of fluorinated, catechol-based, self-assembled monolayers." Langmuir 26.21 (2010): 16211-16220.
Ryu et al. "Bio-inspired adhesive catechol-conjugated chitosan for biomedical applications: A mini review." Acta Biomaterialia 27 (2015): 101-115.
Shafiq et al. "Bioinspired underwater bonding and debonding on demand." Angewandte Chemie 50.18 (2012): 4332-4335.
Shin et al. "Tissue Adhesive Catechol-Modified Hyaluronic Acid Hydrogel for Effective, Minimally Invasive Cell Therapy." Advanced Functional Materials 25.25 (2015): 3814-3824.
Silva-Correia et al. "Gellan gum hydrogels for intervertebral disc tissue-engineering applications." J. Tissue Eng. Regen. Med., 5 (2011) 97-107.
Silva-Correia et al. "Biocompatibility evaluation of ionic-and photo-crosslinked methacrylated gellan gum hydrogels: in vitro and in vivo study." Advanced Healthcare Materials 2.4 (2013): 568-575.

\* cited by examiner

# GELLAN GUM HYDROGELS, PREPARATION, METHODS AND USES THEREOF

CROSS-REFERENCE TO RELATED PATENT APPLICATIONS

This application is a U.S. National Stage Application under 35 U.S.C. § 371 of International Patent Application No. PCT/IB2017/051718, filed Mar. 24, 2017, which claims the benefit of priority under 35 U.S.C. Section 119(e) of Portuguese Patent Application number 109259 filed Mar. 24, 2016, both of which are hereby incorporated by reference in their respective entireties.

TECHNICAL FIELD

The present disclosure relates to modified, bio-inspired gellan gums which form hydrogels having improved physicochemical and biological characteristics suitable for use as standalone medical devices or for cell encapsulation. The modified gellan gum hydrogels containing encapsulated cells may be used for in vitro cell culture or for minimally invasive in vivo delivery and retention of cells and/or active substances and/or biomolecules in tissue engineering, regenerative medicine as well as drug delivery applications. The modified gellan gum hydrogels disclosed herein overcome limitations traditionally associated with existing hydrogel systems, including reproducibility of manufacture, high aqueous solubility and ease of formulation. The modified gellan gums display controllable ionic-crosslinking by a wide range of physiologically relevant cations and possess excellent adhesiveness in situ, whilst maintaining mammalian cells viable during long in vitro culture periods. The modified gellan gum hydrogels further promote up-regulation of the expression of healthy chondrogenic extracellular matrix markers.

The present disclosure also relates to compositions for use in cartilage and soft tissue engineering and regenerative medicine.

BACKGROUND TO THE INVENTION

Cell encapsulation technologies continue to attract increasing attention for a range of in vitro cell culture and screening models as well as for tissue engineering and regenerative medicine applications. In particular, polymers of natural origin including polysaccharides obtained from microbial or marine sources, which are able to form hydrogels under physiologically relevant conditions have been studied extensively as matrices for in vitro cell culture and for the encapsulation and delivery of mammalian cells and/or biomolecules in vivo. Additionally, certain hydrogels may also be applied as standalone products in the form of medical devices in other cell-free tissue engineering applications. Hydrogels are highly hydrated materials composed of hydrophilic polymers which form organized three-dimensional networks upon physical, enzymatic, chemical or ionic crosslinking processes to form soft and porous structures that resemble or mimic the extracellular matrix (ECM) of mammalian tissues. Ease of delivery via minimally invasive procedures, for example by injection, biocompatibility and permeability to allow the continual flux of gases, nutrients and metabolic waste products are all essential requirements for functional cell/biomolecule encapsulation materials. Furthermore, the polymers must be able to undergo hydrogel formation through crosslinking processes which do not compromise cell viability or function, and have the ability to firmly retain the implanted cells and/or biomolecules at the wanted site of action.

To date, a number of hydrogels based on natural polysaccharides and proteins have been investigated as putative cell culture and cell/bioactive encapsulation/delivery agents. These include, amongst others, agarose, alginate, the family of carrageenans, chitosan, hyaluronic acid, collagen, elastin, fibrin, gelatin and silk fibroin. However, the majority of these materials present significant drawbacks which seriously restrict their general applicability for in vitro cell culture, cell delivery or in standalone therapeutic settings in vivo. These include, amongst others, lack of structural consistency and synthetic reproducibility during production or extraction, short and long term physical and metabolic instability, as well as inadequate solubility in physiologically relevant media and pH. In some cases, they also require processing temperatures above physiological temperature incompatible with thermally sensitive therapeutic agents and result in formation of hydrogels with inadequate mechanical properties for specific applications. Furthermore, some of these materials have uncontrolled degradation rates, such that the metabolism and elimination of the biomaterials is not synchronized or compatible with the rate of ECM or tissue production by encapsulated cells and/or biomolecule delivery.

Accordingly, the search continues for more versatile biomaterials for cell and/or biomolecule encapsulation and as standalone medical devices. Recently gellan gum has been proposed as an alternative biomaterial for such purpose (Oliveira, 2009; 2010). Gellan gum is a linear, anionic, extracellular exopolysaccharide secreted by the bacterium *Pseudomonas elodea*, that consists of repeating tetrassaccharide units composed by two D-glucose, one D-glucuronic acid and one L-rhamnose residue [→3)-β-D-Glcp-(1→4)-β-D-GlcpA-(1→4)-β-D-Glcp-(1→4)-α-L-Rhap-(1→].

Commercially, gellan gum is available in two forms, acetylated (high-acyl) and de-acetylated (low-acyl). High-acyl gellan gum contains two acyl substituents, namely acetate (one acetate group for every two repeat units) and glycerate (one glycerate group for every repeat unit) both located on the same glucose residue, while low-acyl gellan gum is produced by basic hydrolysis and typically contains less than 5% acyl substituents to no acyl groups. These two isoforms produce thermo-reversible hydrogels with markedly different mechanical properties upon temperature decrease of solutions in the presence of divalent cations such as Ca2+ and Mg2+. This means that formation of gellan gum hydrogels requires an inconvenient heating/cooling cycle and the presence of divalent cations is essential. Cooling of gellan gum solutions in the presence of only monovalent cations such as sodium (Na+) and potassium (K+) require ionic concentrations approximately 100-times higher to provide hydrogels with similar mechanical properties as those obtained with divalent cations. Such elevated concentrations would be expected to limit encapsulated cell survival due to osmotic shock. On the other hand, gellan gum hydrogels show low cytotoxicity and are relatively stable towards mild heat and dilute acid, but are prone to lose mechanical strength over time due to the diffusion and exchange of the divalent cations responsible for effective crosslinking with physiological monovalent cations within the 3D-matrix when implanted in vivo. Cell encapsulation studies have proven that gellan gum hydrogels are able to support the growth and deposition of ECM by human articular chondrocytes to some degree. Notwithstanding, the considerable hydrophilicity of the negatively charged hydrogel selectively favours binding of water molecules so that the adsorption of cell-adhesive proteins is greatly inhibited at the cell-material surface with the results that cells are unable to attach. The lack of attachment sites or cell adhesion ligands at the polymer surface can be detrimental to the survival and function of adhesion-dependent cells, which can result in decreased cell viability over time and ultimately in poor performance outcomes.

As mentioned, the therapeutic utility of gellan gum hydrogels is hampered further by the low aqueous solubility of the commercially available polymer at physiological temperature (37° C.) or below. Dilute aqueous solutions, typically around 1% w/V concentration, can only be obtained by heating the commercially available low-acyl polymer in water at harsh temperatures, typically around 90° C., for at least one hour. Inconveniently, thermo-reversible gelation occurs when the solution temperature is decreased to around 40-42° C. Obviously, both the dissolution and thermo-gelation temperatures are significantly higher than physiological temperature (37° C.) so that cells are likely to suffer thermal shock upon encapsulation, thereby reducing cell viability and functionality. Premature thermal gelation of gellan gum would also represent a major drawback for a solution to be delivered by injection via a narrow-gauge needle, and thus the narrow temperature window poses serious technical limitations.

A further drawback related to gellan gum relates to its limited adhesiveness to biological tissues and living surfaces, particularly in the presence of bodily fluids and irrigation solutions used during surgical procedures. Since gellan gum hydrogels are highly hydrophilic like most hydrogels, they are unable to effectively adhere to organic or inorganic surfaces (soft or hard tissue) in wet environments. Therefore gellan gum hydrogels delivered or transplanted in vivo are unlikely to be retained at living surfaces once subjected to physical or mechanical stress, thereby seriously reducing their general applicability and effectiveness in therapeutic settings.

Since gellan gum contains one carboxylic acid ($-CO_2H$) functional group for every tetrassaccharide repeat unit courtesy of the glucuronic acid residue, the possibility to chemically modify gellan gum with a view to optimize its physicochemical and biological properties has been explored. Reaction of gellan gum with a large excess of glycidyl methacrylate under slightly basic conditions (Silva-Correia, 2011a) provides methacrylated gellan gum (GG-MA). This very versatile, semi-synthetic material possesses higher aqueous solubility than the parent gellan gum at lower temperatures, so that solutions of 1-2% w/V concentration in water can be obtained at either room or physiological temperature, although the resulting solution viscosity at the higher concentration is in the upper range of that acceptable for delivery by injection, and care must be taken to avoid excessive air entrapment during the dissolution process that may lead to unwanted bubble formation within the hydrogels after crosslinking occurs. Like the parent polymer, GG-MA undergoes ionic-crosslinking promoted by physiologically relevant divalent cations such as $Ca^{2+}$ and $Mg^{2+}$ to form hydrogels. Additionally due to the presence of the $\alpha,\beta$-unsaturated ketone residue on the methacrylate substituent, covalent crosslinking can be effected by exposure of polymer solutions to ultraviolet light in the presence of suitable radical photo-initiators. By varying the polymer concentration and method/degree of crosslinking, GG-MA hydrogels with tunable mechanical properties can be prepared (Silva-Correia, 2011b). Both ionic- and photo-crosslinked GG-MA hydrogels have been shown to be biocompatible and have been used to encapsulate several cell types (Silva-Correia, 2013).

Despite the above mentioned improvements in terms of aqueous solubility and physicochemical properties, GG-MA shares certain limitations with the parent polymer. As stated in WO2011/119059 A1, GG-MA possesses 'some degree of bio-adhesiveness', thereby GG-MA hydrogels are also unlikely to efficiently adhere to biological tissues or surfaces in wet environments and are unlikely to be retained in situ upon application of stress. Furthermore, grafting of the methacrylate substituent does not address the high hydrophilicity issue associated with gellan gum hydrogels, whereby GG-MA hydrogels also do not provide the most appropriate environment for long-term functional behaviour and production of ECM by adherent-dependent cells. Finally, concerns persist with respect loss of mechanical strength over time due to exchange of divalent cations by monovalent cations within the 3D-matrix when implanted in vivo.

Recently, the development of surface-adherent biomaterials has focused on biomimetic approaches. Marine mussels demonstrate impressive adhesion to wet and slippery rock surfaces despite incessant assault by sea waves, due to the production of adhesive proteins at the distal end of their adhesive pads which directly contact the rock surface. Byssal threads connecting the adhesive pads to the mussel contain elevated quantities of an amino-acid known as L-DOPA (3,4-dihydroxy-L-phenylalanine), which contains a catecholamine pharmacophore. The catechol functional group (1,2-dihydroxyphenyl) is responsible for mediating adhesion through a mechanism that involves oxidation of the catechol group to an ortho-quinone, a process that is encouraged by the moderately alkaline pH of seawater. Subsequently, ionic-crosslinking involving the coordination of the ortho-quinone moiety to trivalent metal ions (mainly $Fe^{3+}$) which are amply present in seawater leads to the formation of a sticky, water-resistant glue composed of protein networks. The strength of the ionic coordination bond between the catechol functional group and trivalent ferric ions is deceptively strong. Certain tris- and bis-catechol-$Fe^{3+}$ complexes have some of the highest stability constants of any known metal-ligand chelates and in many cases the force required to break the metal ion-catechol complex is almost comparable that of a covalent bond.

Thus the premise of mimicking natural adhesive mechanisms has been explored with a number of natural polymers with a view to improve the adhesive properties of hydrogels used for cell encapsulation. Catechol-conjugated polymers with tunable physical and mechanical properties have been described for chitosan (Ryu, 2015), alginate (Lee, 2013), polyethylene glycol (PEG) (Barrett, 2013) and hyaluronic acid (Shin, 2015) and mixtures thereof, amongst others. Cell viability data was reported for various cell types encapsulated in catechol-conjugated alginate hydrogels [Huh-7, Neuro-2A, human umbilical vein endothelial cells (HUVEC), human adipose derived stem cells (hASC) and human neural stem cells (hNSC)] and catechol-conjugated hyaluronic acid (human hepatocytes) but only for relatively short culture periods (up to fourteen days and seven days, respectively). However, a further chemical processing step of both polymer-catechol conjugates was necessary before ionic-crosslinking with metal cations could occur, involving sodium periodate oxidation of the catechol functionality. Besides the inconvenience of this extra synthetic processing step, the hydrogels thus formed were very highly coloured (brown-black) due to the formation and polymerization of the resulting ortho-quinone. Preferably, for use as in vitro cell culture agents, tissue bio-adhesives or cell delivery matrices in tissue engineering and regenerative medicine applications, transparent, colourless hydrogels would be preferable as these would allow visual confirmation of homogenous dispersion of cells within the matrix upon mixing the biomaterial and cell suspension components, as well as to facilitate monitoring of biological events by imaging and biochemical assays. In the case of PEG-catechol conjugates, hydrogels were formed exclusively with trivalent ferric ions (Fe3+), and the pH had significant impact on the mechanical properties of the hydrogels formed.

Functionalization of the catechol ring of polymer-catechol conjugates by further incorporation of a strongly electron-withdrawing nitro group and the effects of the nitro-group substitution on crosslinking and bio-adhesive properties of certain hydrogels has been reported (Shafiq, 2012; Cencer, 2015 and Ding, 2015).

AU2011381641 B2 discloses the preparation of a catechol group-coupled chitosan which is included in a composition with a poloxamer containing a thiol group as a bio-adhesive agent having hemostatic effect.

EP2784101 A1 discloses a hydroxyphenyl functionalized poly(ester amides) with bio-adhesive properties.

U.S. Pat. No. 8,968,716 B2 discloses catechol-modified polymers which form hydrogels in situ through enzymatic reaction, for use as tissue adhesives.

WO2015175655A1 discloses catechol modified polymers as tissue adhesives or anti-fouling coatings.

WO2013/123946 discloses self-healing, pH-responsive catechol-modified polymers and gel compositions. Selective tuning of mechanical properties was claimed, however no details on favourable cell encapsulation properties or biological response are revealed.

From the literature, existing biomaterials present physicochemical and/or biological limitations for both in vitro cell culture and tissue engineering and regenerative medicine applications. The design of improved biomaterials for such purposes should consider various factors; (i) reproducibility in terms of consistent quality (ii) hydrogel precursors should be endowed with good aqueous solubility facilitating rapid dissolution at relevant concentrations at or below physiological temperature, (iii) hydrogel precursors should be able to form mechanically stable, tissue or surface-adhesive and practically colourless hydrogels without the requirement for further intermediate chemical or production steps to introduce crosslinking functionality into the molecule and (iv) ionic-crosslinking should be possible with a wide range of monovalent, divalent and trivalent metal ions that are both pharmaceutically acceptable and physiologically relevant. Finally, a most desirable hydrogel system should be able to sustain viability of encapsulated cells and functionality of biomolecules over extended periods and promote up-regulation of the expression of healthy extracellular matrix markers.

These facts are disclosed in order to illustrate the technical problem addressed by the present disclosure.

GENERAL DESCRIPTION

The present disclosure provides novel gellan gum-based materials comprising gellan gum modified with phenolic or catecholic groups or isosteres thereof capable of forming hydrogels by chelating monovalent, divalent and/or trivalent metal ions. These gellan gum hydrogels are endowed with improved physicochemical and biological characteristics for in vitro cell culture and/or the encapsulation and in vivo delivery/retention of mammalian cells and/or biomolecules for application in tissue engineering and regenerative medicine. The modified gellan gum hydrogels overcome the limitations traditionally associated with current hydrogel systems, including ease of formulation and injectability, rapid dissolution, multiple ionic-crosslinking modes, sustained mechanical properties over time and greater adhesiveness in situ, whilst maintaining mammalian cells viable during long culture periods and promoting the up-regulation of expression of healthy extracellular matrix markers and tissue regeneration.

In a preferred embodiment, the modified gellan gum acylation degree is from no acyl groups (low-acyl) up to two acyl substituents (high-acyl), namely acetate and glycerate, both located on the same glucose residue, more preferably one glycerate substituent per repeat unit and one acetate substituent per every two repeat units. Preferably, the gellan gum contains from less than 5% acyl groups to no acyl groups.

In an embodiment, commercial gellan gum (GGc) may be used as the starting material for the preparation of the modified gellan gum hydrogels described herein. Preferably the commercial gellan gum is low-acyl gellan gum. In a more preferred embodiment, the hydrogel precursor materials are prepared using purified gellan gum (GGp) as the starting material (Doner, 1997). Commercial gellan gum contains divalent cation impurities as well as inorganic ash which can be removed by treatment with an appropriate ion exchange resin in acid form, converting the gellan gum to an intermediate free carboxylic acid form. Treatment of this intermediate free carboxylic acid form of gellan gum with a dilute aqueous alkali metal hydroxide solution, such as aqueous sodium hydroxide, potassium hydroxide or lithium hydroxide leads to the formation of the corresponding monovalent alkali metal salt forms of gellan gum which are considerably more soluble in water at room temperature at concentrations up to 5% w/V, making this form of the polymer more suitable for further structural manipulation via synthetic organic chemistry under aqueous conditions. Purified gellan gum forms hydrogels in the presence of divalent and trivalent cations, but fails to form mechanically stable hydrogels in the presence of monovalent ions only. Thus purified gellan gum hydrogels used as controls in biological studies were prepared using the divalent cations $Ca^{2+}$ and $Mg^{2+}$ as crosslinking agents.

Alternatively, the intermediate free carboxylic acid form of gellan gum may be treated with ammonium hydroxide or a tetraalkylammonium hydroxide to form the corresponding ammonium salt forms of gellan gum. Such salts have the advantage of being soluble in polar organic solvents such as N,N-dimethylformamide, N,N-dimethylacetamide, N-methylpyrrolidinone and DMSO, amongst others, making these ammonium salt forms of the polymer more suitable for further structural manipulation via synthetic organic chemistry under non-aqueous conditions.

In an embodiment, by varying the molecular weight of the purified gellan gum starting material, the modified gellan gums may be obtained with a range of molecular weights ranging from 100 KDa to 2500 KDa, in order to allow control over the physiochemical and mechanical properties and tailor the crosslinking kinetics of the modified gellan gums. Methods to reduce the molecular weight of gellan gum are well known to those skilled in the art. For example, U.S. Pat. No. 6,242,035 describes several methods for reducing the molecular weight of gellan gum, including homogenization, sonication, radiation, oxidation and hydrolysis. Hydrolysis catalyzed by acid is a particularly well known technique used to reduce the molecular weight of polysaccharide-based polymers. Under more extreme hydrolytic conditions, polyssacharides may be broken down into oligosaccharides and the constituent sugars. By using organic and inorganic acids such as sulphuric acid, hydrochloric acid, acetic acid and trifluoroacetic acid amongst others, at different concentrations and reaction temperatures, it is possible to obtain gellan gum with a range of molecular weights. Alternatively, the molecular weight of gellan gum may be reduced via chemical scission of the polymer backbone using an oxidizing agent such as sodium periodate, peroxides or 2,2,6,6-tetramethylpiperidine-N-oxyl (TEMPO). Gellan oxidation by sodium periodate is particularly effective for obtaining a range of reduced molecular weight gellan gum (Gong, 2009). Alternatively, an enzymatic method based on an extracellular gellan lyase from the Bacillus sp. GL1 bacterium may be employed to reduce the molecular weight of gellan gum (Hashimoto, 1999).

In a preferred embodiment, the modified gellan gum has a molecular weight between 100 and 2500 KDa, more preferably between 500 and 2500 KDa and even more preferably between 1000 and 2500 KDa.

In a preferred embodiment, the unit attached to gellan gum capable of chelating monovalent, divalent and/or trivalent ions is a phenolic or catechol unit or an isostere thereof. A phenolic group is a carbocyclic aromatic ring containing one hydroxyl group and a catechol is a carbocyclic aromatic ring containing two adjacent hydroxyl groups. If preferred, the phenolic or catechol units may be further substituted on the aromatic ring by one or more, or combinations of the following groups: $C_1$-$C_6$ lower alkyl groups (methyl, ethyl, propyl, isopropyl, isobutyl, pentyl and hexyl); hydroxyl, nitro, cyano, trifluoromethyl or halogen groups (fluorine, chlorine, bromine, iodine); lower alkoxy groups —$OR_1$ wherein $R_1$ signifies a $C_1$-$C_6$ lower alkyl group as defined above; the group —C(O)—$R_2$, where $R_2$ signifies hydrogen or a $C_1$-$C_6$ lower alkyl group as defined above; the group —C(O)—$OR_3$ where $R_3$ signifies hydrogen or a $C_1$-$C_6$ lower alkyl group as defined above; the group —C(O)$NR_4R_5$ wherein $R_4$ and $R_5$ signify hydrogen or $C_1$-$C_6$ lower alkyl groups as defined above or the group —$SO_2R_6$ where $R_6$ signifies hydrogen or a $C_1$-$C_6$ lower alkyl groups as defined above.

In an embodiment, the phenolic or catechol unit may be covalently attached to gellan gum directly via a heteroatom, which may be either oxygen or optionally substituted nitrogen or alternatively via a heteroatom and a spacer or linker group. Suitable examples of linker groups include, but are not restricted to $C_1$-$C_{18}$ lower alkyl groups (methyl to octadecyl), linked to the carboxylic acid functional group of gellan gum via a heteroatom, which may be either oxygen or optionally substituted nitrogen. If preferred, the $C_1$-$C_{18}$ alkyl linker groups may linear or branched, optionally be further substituted and optionally incorporate one or more heteroatoms chosen from nitrogen, oxygen or sulphur. In another embodiment, the C1-C18 linker group may optionally contain unsaturated carbon-carbon bonds.

In a most preferred embodiment, a phenolic or catecholic unit is covalently attached to the carboxylic acid functional group gellan gum via an amide nitrogen heteroatom and an ethyl group linker (—$NH(CH_2)_2$-catechol or phenol).

In an embodiment, examples of well-known catechol isosteres capable of chelating monovalent, divalent and trivalent metal cations include saturated or unsaturated aliphatic, carbocylic or heterocyclic groups containing orthogonal ketone, amino, or hydroxyl functionalities, such as, for example, tropolones, quinolinones, pyrones, pyridinones and pyrimidones. Other possible catechol isosteres will be well known to the skilled artisan.

In a particularly preferred embodiment, catechol isosteres include 3-hydroxy-4-pyridinones or 5-hydroxypyrimidone-4(3H)-ones.

In a preferred embodiment, the modified gellan gum containing a phenol or catechol unit or isostere thereof is capable of undergoing ionic-crosslinking in the presence of one or more monovalent, divalent and/or trivalent metal ions, or mixtures thereof, including $Na^+$, $K^+$, $Li^+$, $Ca^{2+}$, $Mg^{2+}$, $Fe^{2+}$, $Cu^{2+}$, $Sr^{2+}$, $Ba^{2+}$, $Co^{2+}$, $Mn^{2+}$, $Ni^{2+}$, $Sn^{2+}$, $Zn^{2+}$, $Fe^{3+}$, $Al^{3+}$, $Ga^{3+}$ and $Ti^{3+}$ ions.

In another preferred embodiment, the modified gellan gum containing a phenol or catechol unit is capable of undergoing enzymatic crosslinking, for example in the presence of horseradish peroxidase and hydrogen peroxide.

In yet another preferred embodiment, the modified gellan gums described herein are completely soluble in water, or other physiologically acceptable vehicle at room or physiological temperature (15-37° C.) at concentrations between 0.01-5% w/V, more preferably between 1-3% w/V. Even more preferably, the modified gellan gums are soluble in water or physiologically acceptable vehicle at room temperature thirty minutes or less. Modified gellan gum solutions possess viscosities more suitable for injection through a range of needle gauges (7-34).

The present disclosure relates to a modified gellan gum from which hydrogels can be prepared by ionic-crosslinking or enzymatic crosslinking of a modified gellan gum having a composition according to Formula I:

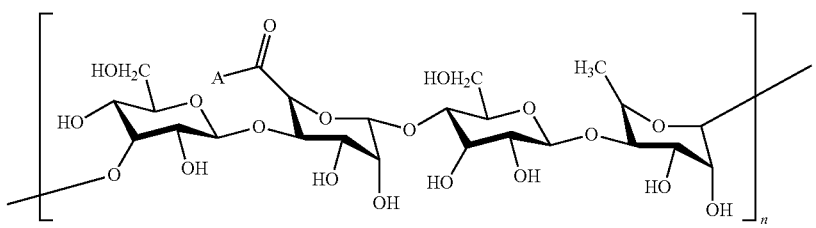

Formula I wherein n is an integer from 1-4000, preferably from 50 to 4000, more preferably from 500 to 4000, A signifies the group —O—$R_7$ or —N—$R_7R_8$ wherein $R_7$ signifies a group according to Formula II:

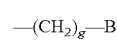

Formula II wherein g is an integer from 0 to 18

B represents a phenolic or catechol group optionally substituted on the aromatic ring by one or more, same or combinations of the following groups: $C_1$-$C_6$ alkyl groups (methyl, ethyl, propyl, isopropyl, isobutyl, isopentyl, isohexyl); hydroxyl, nitro, cyano, trifluoromethyl or halogen groups (fluorine, chlorine, bromine, iodine); alkoxy groups —$OR_1$ wherein $R_1$ signifies a $C_1$-$C_6$ alkyl group as defined above; the group —C(O)—$R_2$, where $R_2$ signifies hydrogen or a $C_1$-$C_6$ alkyl group as defined above; the group —C(O)—$OR_3$ where $R_3$ signifies hydrogen or a $C_1$-$C_6$ alkyl group as defined above; the group —C(O)$NR_4R_5$ wherein $R_4$ and $R_5$ signify hydrogen or $C_1$-$C_6$ alkyl groups as defined above or the group —$SO_2R_6$ where $R_6$ signifies hydrogen or a $C_1$-$C_6$ alkyl groups as defined above; or B represents a 3-hydroxy-4-pyridinone or 5-hydroxypyrimidone-4(3H)-one group; and $R_8$ signifies hydrogen or a $C_1$-$C_6$ alkyl group chosen from methyl, ethyl, propyl, isopropyl, butyl, isobutyl, pentyl, isopentyl or hexyl.

In another preferred embodiment, the invention relates to a modified gellan gum from which hydrogels can be prepared by ionic-crosslinking or enzymatic crosslinking of a modified gellan gum having a composition according to Formula III;

n is an integer from 1-4000, preferably from 50 to 4000, more preferably from 500 to 4000, and $R_9$, $R_{10}$, $R_{11}$ and $R_{12}$ are the same or different, and signify hydrogen, hydroxyl, $C_1$-$C_6$ alkyl groups (methyl, ethyl, propyl, isopropyl, isobutyl, isopentyl, isohexyl); nitro, cyano, trifluoromethyl or halogen groups (fluorine, chlorine, bromine, iodine); alkoxy groups —$OR_1$ wherein $R_1$ signifies a $C_1$-$C_6$ alkyl group as defined above; the group —C(O)—$R_2$, where $R_2$ signifies hydrogen or a $C_1$-$C_6$ alkyl group as defined above; the group —C(O)—$OR_3$ where $R_3$ signifies hydrogen or a $C_1$-$C_6$ alkyl group as defined above; the group —C(O)$NR_4R_5$ wherein $R_4$ and $R_5$ signify hydrogen or $C_1$-$C_6$ alkyl groups as defined above or the group —$SO_2R_6$ where $R_6$ signifies hydrogen or a $C_1$-$C_6$ alkyl groups as defined above.

In an even more preferred embodiment, the invention relates to a modified gellan gum from which hydrogels can be prepared by ionic-crosslinking or enzymatic crosslinking of a gellan gum having a composition according to Formula IV;

Formula III

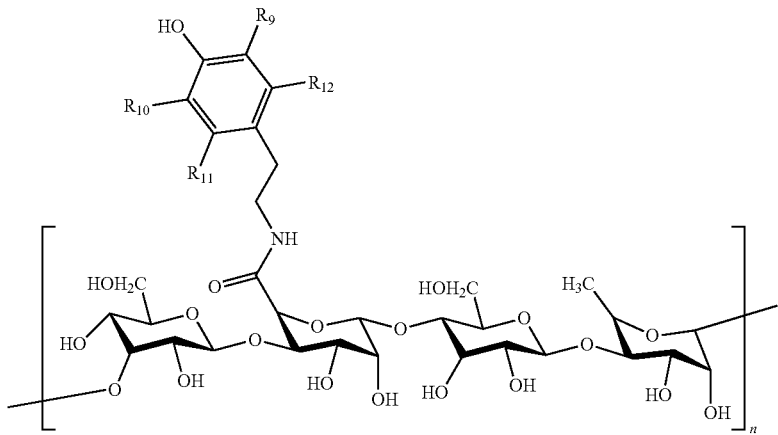

wherein

Formula IV

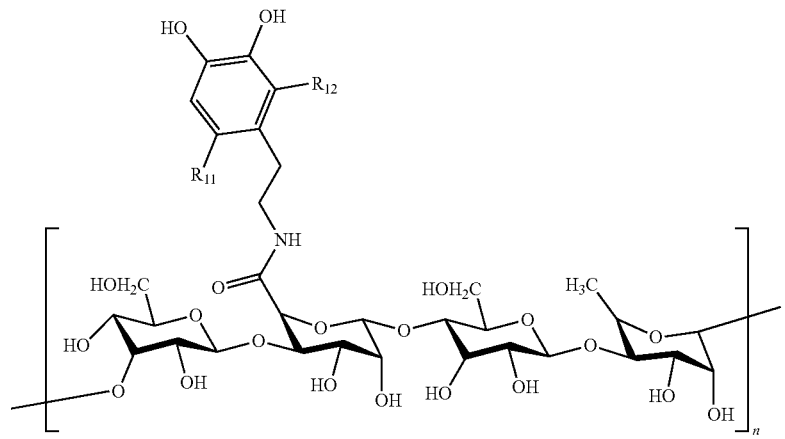

wherein:

n is an integer from 1-4000, preferably from 50 to 4000, more preferably from 500 to 4000, $R_{11}$ and $R_{12}$ are the same or different and signify hydrogen, nitro, cyano or halogen (fluorine, chlorine, bromine, iodine).

In a most preferred embodiment, the invention relates to a modified gellan gum from which hydrogels can be prepared by ionic-crosslinking or enzymatic crosslinking of a modified gellan gum having the composition according to Formula V;

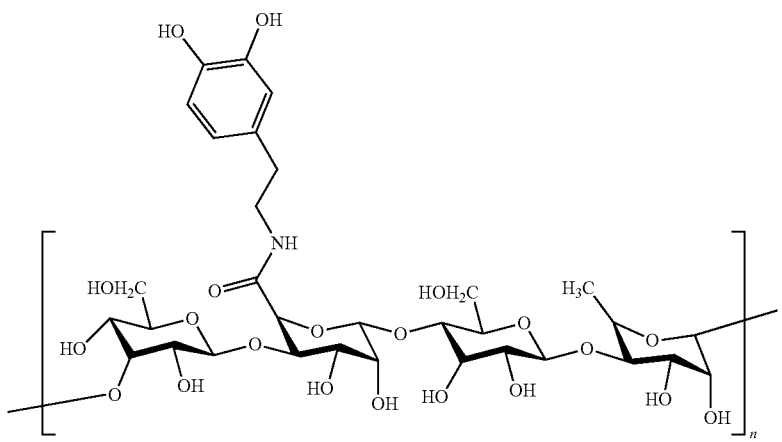

Formula V n is an integer from 1-4000, preferably from 50 to 4000, more preferably from 500 to 4000.

In an embodiment, C1-C6 alkyl group is selected from the group consisting of: methyl, ethyl, propyl, isopropyl, butyl, isobutyl, pentyl, isopentyl, hexyl or isohexyl.

In an embodiment, the halogen group is selected from the group consisting of: fluorine, chlorine, bromine or iodine.

In an embodiment, the gellan gum may be enzymatically crosslinkable, in particular by horseradish peroxidase and hydrogen peroxide.

In an embodiment for better results, the gellan gum of the present disclosure is used in human or veterinary medicine or as a medicament or use in vitro cell culture. Preferably, the gellan gum of the present disclosure is used in tissue engineering or regenerative medicine. More preferably, the gellan gum of the present disclosure is used in microfracture, or treatment or therapy of bone, cartilage or soft tissue diseases or lesions. Even more preferably, for use in the treatment or therapy of hyaline cartilage damage, in particular knee cartilage injury. Even more preferably, the gellan gum of the present disclosure is used for chondrogenic and/or osteogenic and/or adipogenic differentiation of human mesenchymal stem cells.

In an embodiment for better results, the gellan gum of the present disclosure may be used in the treatment or therapy of a disease that is positively influenced by the chondrogenic and/or osteogenic and/or adipogenic differentiation of human mesenchymal stem cells.

In an embodiment for better results, the gellan gum of the present disclosure may be used in bone repair and microfracture.

In an embodiment for better results, the gellan gum of the present disclosure may be used in the treatment or therapy of bone fracture, bone repair or in the treatment of osteopathies or in the treatment of osteochondritis.

In an embodiment for better results, the gellan gum of the present disclosure may be used in intradermal and transdermal therapies.

In an embodiment, the modified gellan gums having compositions according to Formulas I, III, IV and V may be prepared by reacting commercial gellan gum (GGc) or purified gellan gum (GGp) with appropriately substituted alcohols or appropriately substituted primary and secondary amines in the presence of suitable coupling agents well known to the skilled artisan to promote activation of carboxylic acids for reaction with oxygen or nitrogen nucleophiles to form esters and amides, respectively. Suitable coupling agents include carbodiimides such as dicylohexylcarbodiimide (DCC) or 1-ethyl-3-(3-dimethylaminopropyl)carbodiimide hydrochloride (EDC) with, or without, additives such as hydroxybenzotriazole (HOBt) or N-hydroxysuccinimide (NHS), phosphonium salts such as benzotriazol-1-yloxytris(dimethylamino)-phosphonium hexafluorophosphate, guanidinium and uranium salts such as (2-(1H-benzotriazol-1-yl)-1,1,3,3-tetramethyluronium hexafluorophosphate and N,N,N',N'-tetramethyl-O-(benzotriazol-1-yl)uronium tetrafluoroborate and triazines such as cyanuric chloride and 2-chloro-4,6-dimethoxy-1,3,5-triazine (CDMT) in conjunction with N-methylmorpholine, amongst others. Particularly preferred coupling agents include 4-(4,6-dimethoxy-1,3,5-triazin-2-yl)-4-methylmorpholinium chloride (DTMMCl). Surprisingly, it has been found that DTMMCl may be used as the coupling agent for the reaction of purified gellan gum with primary and secondary amines in salt form (hydrochloride, hydrobromide) without the need for addition of a non-nucleophilic base such as triethylamine, diisopropylamine or DBU to release the reactive free base form of the primary and secondary amines. This is particularly important in the case of amines such as dopamine, which is highly reactive in the free-base form such that it rapidly self-condenses to form intensely coloured polydopamine, which imparts undesired dark colour to the dopamine-modified gellan gums. By using DTMMCl as the coupling agent when using dopamine hydrochloride, the use of a slight excess of added base relative to the amine salt is not required, and the modified gellan gums are obtained as white to off-white powders.

Another aspect of the present disclosure relates to a hydrogel comprising the modified gellan gum of the present disclosure and a suitable solvent, in particular an aqueous solution. Preferably, the suitable solvent is water, a cell culture media, an aqueous saline solvent, or mixtures thereof.

In an embodiment for better results, the concentration of the gellan gum of the present disclosure may be between 0.01% and 5% w/V, preferably 0.5%-5% w/V, more preferably 0.5%-2.5% w/V, even more preferably 1.25%-2% w/V.

Another aspect of the present disclosure relates to a composition comprising the gellan gum or the hydrogel of the present disclosure and a bioactive ingredient selected from the group consisting of a cell, a stem cell, a protein, a biomolecule, a small molecule active substance, a therapeutic agent or a diagnostic marker, or mixtures thereof.

In an embodiment for better results, the cell or stem cell are selected from a group consisting of: mammalian chondrocytes, mammalian mesenchymal stromal/stem cells, mammalian bone marrow mesenchymal stem cells, or mixtures thereof.

In an embodiment for better results, the composition may comprise mammalian cells and a physiological ionic solution comprising cations in an effective amount for ionic crosslinking.

In an embodiment for better results, the composition may further comprise a bone marrow aspirate concentrate, growth factors and/or antibiotics.

In an embodiment for better results, the composition may further comprise a matrix containing the gellan gum of the present disclosure or the hydrogel of the present disclosure and human adipose mesenchymal stromal/stem cells.

In an embodiment for better results, the cell may be encapsulated within the gellan gum, preferably an autologous cell.

In an embodiment for better results, the growth factor may be TGF-β1, bone morphogenetic protein-2 (BMP-2), BMP-7 (also known as osteogenic protein-1 [OP-1]) or cartilage-derived morphogenetic proteins CDMP-1 and CDMP-2, platelet lysates, or mixtures thereof.

The compositions can be administered by various routes, including topical, enteral and parenteral. Parenteral administration routes include intra-arterial, intra-articular, intracavitary, intradermal, intralympathic, intramuscular, intrasynovial, intravenous, and subcutaneous. Enteral routes include oral and gastro-intestinal. Topical routes include application onto the skin and mucous membranes.

In a preferred embodiment, the composition is delivered to a patient in injectable form or transdermal form, namely an in situ injection or a transdermal therapeutic system, more preferably a patch.

Another aspect of the present disclosure relates to a mesh, disk, scaffold, three-dimensional structure, strip, net, gauze or membrane comprising the gellan gum of the present disclosure or the hydrogel of the present disclosure, or the composition of the present disclosure.

A transdermal therapeutic system, in particular a patch, comprising the gellan gum of the present disclosure or the hydrogel of the present disclosure, or the composition of the present disclosure.

A kit for use in use in tissue engineering, regenerative medicine, or in vitro cell culture comprising the gellan gum of the present disclosure or the hydrogel of the present disclosure, or the composition of the present disclosure and mammalian cells.

Thus another aspect of the present disclosure comprises the method for preparation of uncoloured modified gellan gums according to Formulas I, III, IV and V by reacting a purified gellan gum according to Formula VI;

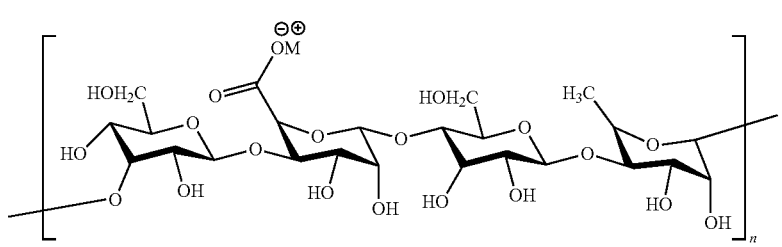

Formula VI wherein:

n is an integer from 1-4000, preferably from 50 to 4000, more preferably from 500 to 4000, $M^+$ signifies a monovalent alkali metal ion chosen from the group $Na^+$, $K^+$ and $Li^+$; or $M^+$ signifies the group $N^+X_4$ wherein X signifies hydrogen or a C1-C4 alkyl group (methyl, ethyl, propyl, butyl), with a primary, secondary or tertiary alcohol, primary amine or secondary amine having the formula $HO-R_7$ or $HN-R_7R_8$, wherein $R_7$ and $R_8$ are defined above, and the reaction is conducted in the presence of at least one coupling agent and optionally in the presence of a non-nucleophilic base.

The coupling of commercial or purified gellan gum with alcohols and amines to give the gellan gum hydrogels of Formula I, III and IV can be carried out in water, distilled or sterile water, or in polar organic solvents such as N,N-dimethylformamide, N,N-dimethylacetamide, N-methylpyrrolidinone and dimethlsulphoxide (DMSO), or in buffered media such as aqueous solutions of 2-(N-morpholino)ethanesulfonic acid (MES) or phosphate buffered saline (PBS), if pH control of the reaction is considered desirable. If preferred, the coupling reaction may be carried out in mixtures of water and one or optionally more polar organic solvents.

In an embodiment for better results, the coupling of commercial or purified gellan gum with alcohols and amines may be carried out in the presence of a non-nucleophilic base. Suitable non-nucleophilic bases include alkylamines such as triethylamine, tributylamine and N,N-diisopropylethylamine (Hunig's base), cyclic amines such as 1,8-diazabicyclo[5.4.0]undec-7-ene (DBU) and N-methylmorpholine, and aromatic amines such as pyridine, 2,2,6,6-tetramethylpiperidine, 2,6-dimethylpyridine and collidine, amongst others.

In an embodiment for better results, the coupling reactions of gellan gum with alcohols and amines may be carried out at a temperature between 0° C. and the boiling point of the solvent, preferably between 10 and 60° C. and even more preferably between 15 and 40° C.

In an embodiment for better results, the modified gellan gums of the present disclosure may be recovered from the reaction mixtures by precipitation of the product by addition of one to 50 volumes of a water-miscible organic solvent including alcohols such as methanol, ethanol or isopropanol, ketones such as acetone or dialkyl ethers such as diethyl ether or diisopropyl ether, followed by phase separation by filtration. If desired, the modified gellan gum thus obtained may be purified further by repeated reconstitution in water and precipitation.

In an embodiment for better results, the precipitated modified gellan gums of the present disclosure may be solubilised in water and purified by dialysis against water using cellulose membranes with appropriate pore size to allow diffusion of low molecular weight contaminants. Alternatively, purification may be achieved via ultrafiltration using for example cellulose or polyethersulphone membranes having appropriate pore size to allow passage of said contaminants.

In an embodiment for better results, the aqueous solutions containing modified and purified gellan gums may then be rendered sterile (absence of bacterial microorganisms and endotoxins), for example by filtration through a 0.22 μm pathogen-free polyethersulphone membrane, by applying vacuum or pressure.

In an embodiment for better results, the modified gellan gums of the present disclosure may be isolated by first freezing the solutions at temperatures between 0 to −210° C., preferably between −20 to −80° C., followed by lyophilisation (freeze-drying) at temperatures between −40 to −90° C. under vacuum at pressures around 0.01 mbar. Alternatively, the modified gellan gums may be isolated by spray-drying of the solutions. By careful choice of spray-drying conditions, modified gellan gums with various particle sizes may be obtained. If preferred, spray-drying may be used in conjunction with antibiotics, medical ingredients and additives to form gellan gum encapsulated or loaded materials.

In an embodiment for better results, sterilization methods of the modified gellan gums in solution or in the solid state include moist or dry heat, exposure to ethylene oxide, contact with supercritical fluids such as carbon dioxide at suitable pressures and temperatures, optionally in the presence of a co-solvent such as an alcohol including methanol, ethanol or isopropanol, or a peroxide such as hydrogen peroxide or peroxyacetic acid, or UV or gamma-irradiation, amongst others.

The thus obtained modified gellan gums may be characterised in terms of structure by analytical techniques such as nuclear magnetic resonance (NMR) spectroscopy. This technique can also be used to determine the degree of substitution of the modified gellan gums by the ion-chelating phenolic and catecholic substituents, by application of a mathematical equation based on the integration of selected reference peaks (Hamcerencu, 2008).

In an embodiment, by selection of appropriate reaction temperature, reagent stoichiometry and reaction times, it is possible to obtain different degrees of substitution of the gellan gum, allowing for tailoring of physicochemical, mechanical and biological properties of the modified gellan gums for specific applications. Preferably, the degree of substitution of gellan gum is between 0.01-30%, more preferably 0.1-20% and most preferably 0.5-15%. As mentioned in the previous paragraph, the degree of substitution may be calculated using the equation reported in the literature for ester derivatives of gellan gum (by NMR spectroscopy described in chapter 2.4 of Hamcerencu, 2008).

In an embodiment for better results, the modified gellan gums of the present disclosure are stable substances in air and at physiological (37° C.) and room temperatures (20° C.) and below, that may be provided in compositions in the form of powders, aqueous solutions, or sterile injectable solutions in pharmaceutically acceptable vehicles such as sterile water for injection, saline or phosphate buffered saline and the like.

In an embodiment for better results, the modified gellan gums of the present disclosure gums have a low polydispersity index (Mw/Mn), preferably <3 and more preferably <2.5. The polydispersity index may be determined by gel permeation or size-exclusion chromatography. For this purpose, a Malvern Viscotek TDA 305 refractometer may be used, equipped with right angle scattering and viscometer detectors typically on a set of four columns, with refractive index detection (RI-Detector 8110, Bischoff). The system may be kept at 30° C. and MilliQ water or other suitable solvent is used as eluent at a flowrate of around 1 mL/min. Elution times and the RI detector signal can be calibrated with a commercial polysaccharide set that contains standards with narrow polydispersity and Mp (molecular mass at the peak maximum) ranging from 180 Da to 708 KDa.

In an embodiment for better results, the modified gellan gums of the present disclosure may be used as either acellular or cellular systems for in vitro and in vivo applications, can be dispensed manually or automatically using computer assisted systems, may be delivered to the human/animal body by minimally invasive procedures such as injection, and are ionically crosslinked directly at the desired site of action by physiologically relevant cations, or alternatively by other pharmaceutically acceptable cation additives to the preparation.

In an embodiment for better results, the modified gellan gums of the present disclosure may be mixed with a biologically active or therapeutic agent in a pharmaceutically acceptable amount for site-directed delivery and retention. In a preferred embodiment, the biological or therapeutic agent is a cell, a stem cell, a protein, diagnostic marker or small molecule active substance, or a mixture thereof. Where the biological or therapeutic agent is a cell, the cell may be autologous or allogeneic.

In an embodiment for better results, the cells may relate to cartilage forming cells. In a preferred embodiment, the cells relate to pluripotent or multipotent stem cells. In a more preferred embodiment, cells relate with adult mesenchymal stromal/stem cells. In a preferred embodiment, cells are obtained from bone marrow or adipose tissue, which can be used immediately after isolation from the patient or sourced alternatively from a Master Cell Bank or from a Working Cell Bank. In this case, the donor of said cells has also been qualified in terms of relevant factors such as age, body mass index, absence of bloodborne pathogens, presence/absence of any specific medical condition. In a preferred embodiment, cells have been qualified for sterility, viability, and expression of mesenchymal stromal/stem cell markers. In a more preferred embodiment a sub-population of chondrogenic progenitor cells is selected from the initial stromal/stem cells, such as cells expressing, but not limited to, CD73, CD106, CD271, CD29, SOX-9, dlk1/FA1, CD44 and CD151 markers. In a preferred embodiment, cells are expanded in xeno-free cell culture media to reach required number of cells, which are used at a passage between 1 and 10, preferably at a passage between 2 and 5.

In an embodiment for better results, the modified gellan gums of the present disclosure may be mixed with chondrocytes alone or with chondrocytes in combination with mesenchymal stromal/stem cells. Alternatively, the modified gellan gums may be mixed with cells selected from: embryonic stem cells, fetal stem cells, adult stem cells, amniotic stem cells, induced pluripotent stem cells, cells of the ectoderm lineage, including astrocytes, boettcher cells, choroid plexus cells, epithelial cells, claudis cells, columnar cells, cone photoreceptors, dark cells, duct cells, ependymal cells, epithelial cells, gland cells, hair cells, hyalocytes, interdental cells, keratinocytes, lens fibre cells, light cells, merkel cells, muller cells, myoepithelial cells, neurons, oligodendrocytes, phalangeal cells, pillar cells, pineal interstitial cells, pinealocytes, pituicytes, pituitary cells, planum semilunatum cells, rod cells, sebaceous gland cells, secretory cells, squamous cells, stellate cells, stria vascularis cells, supporting cells, tanycytes, type i taste bud cell, vestibular apparatus membrane cell, cells of the endoderm lineage, including acinar cells, alpha cells, argentaffin cells, beta cells, brush border cells, centroacinar cells, chromophobic cells, ciliated respiratory tract cells, clara cells, delta cells, duct cells, epithelial cells, gastroenteropancreatic cells, gland cells, hepatocytes, oxyntic cells, paneth cells, pneumocytes, principal (chief) cells, pulmonary endocrine cells, secretory stomach cells, thymic epithelial-reticular cells, thymocytes, thyroid follicular cells, zymogenic cells, cells of the mesoderm lineage, including adipose cells, brush border cells, cementoblasts, chondroclasts, ciliated reproductive cells (male and female), corpus luteum cells, dendritic cells, duct cells, endothelial cells, epithelial cells, erythrocytes, fibroblastic reticular cells, follicle cells, gland cells, interstitial cells, kupffer cells, langerhans cell, leukocytes, leydig cells, littorial cells, lymphocytes, macrophages, macula densa cells, mast cells, megakaryocytes, mesangial cells, mesothelial cells, microglia, monocytes, osteoclasts, osteoblasts, muscle cells, myofibroblasts, non-ciliated cells, nucleus pulposus cells, parietal cells, peripolar cells, plasma cells, plasmacytoid dendritic cells, epididymis principal cells, purkinje fibre cells, secretory cells, serosal cells, sertoli cells, tenocytes, testis interstitial cells, theca interna cells, zona fasciculata, glomerosa and reticularis cells, podocytes, chondrocytes, pericytes, osteocytes, fibroblasts, synovial cells, cells of the neural crest lineage, including carotid body type i cells, chromaffin cells, enteric glial cells, epithelial cell, melanocytes, myoepithelial cells, neurons, odontoblasts, parafollicular cells, satellite cells, schwann cells, small intensely fluorescent cells, squamous cells, carotid body type ii cells and secretory cells, or mixtures thereof.

In an embodiment for better results, the modified gellan gums may be mixed with, or encapsulate, a biologically active or therapeutic agent in a pharmaceutically acceptable amount for site-directed delivery and retention via topical, enteral or parenteral routes, such as for example ocular, nasal, auricular, sub-lingual, rectal, vaginal or dermal administration, as a means to improve the bioavailability of the substance and/or release profile in order to improve overall efficacy. The biological or therapeutic agent in this context is defined as a drug or cosmetic agent directed to enhancing, modifying or maintaining a biological or physiological functionality. For example, the biologically active or therapeutic agent may comprise α-adrenergic agonists; β-adrenergic agonists; α-adrenergic blockers; β-adrenergic blockers; alcohol deterrents; aldose reductase inhibitors; aldosterone antagonists; amino acids; anabolics; analgesics; anesthetics; anorexics; antacids; anthelmimetics; anti-acne agents; anti-allergics; anti-androgens; anti-anginal agents; anti-anxiety agents; anti-arrythmics; anti-asthmatics; antibacterial agents and antibiotics; anti-alopecia and antibaldness agents; anti-amebics; antibodies; anticholinergic drugs; anticoagulants and blood thinners; anticolitis drugs; anticonvulsants and anti-epileptic drugs; anticystitis drugs; antidepressants; antidiabetic agents; antidiarrheal agents; antidiruetics; antidotes; anti-emetics; anti-estrogens; antiflatulents; antifungal agents; antigens; antiglaucoma agents; antihistaminics; antihyperactives; antihyperthyroid agents; antihyperlipoproteinemetics; antihypertensives; antihypotensives; anti-infectives; anti-inflammatory agents (steroidal and non-steroidal); antimalarials; antimigraine agents; antineoplastics; anti-obesity agents; antiparkinsonian agents; antidyskinetics; antpneumonia agents; antiprotozoal agents; antipruritics; antipsoriatics; antipsychotics; antipyretics; antiheumatics; antisecretory agents; antishock medications; antispasmodics; antithrombotics; antitumour agents; antitussives; anti-ulceratives; antiviral agents; anxiolytics; bactericidins; bone densifiers; bronchodilators; calcium channel blockers; carbonic anhydrase inhibitors; cardiotonics and heart stimulants; chemotherapeutics; choloretics; cholinergics; chronic fatigue syndrome medications; CNS stimulants and depressants; coagulants; contraceptives; cystic fibrosis medications; decongestants; diuretics; dopamine receptor agonists and antagonists; enzymes, estrogens; expectorants; gastric hyperactivity medications; glucocorticoids; hemostatics; HMG CoA reductase inhibitors; hormones; hypnotics; immunomodulators; immunosuppressants; laxatives; medicaments for oral and periodontal diseases; miotics; monoamine oxidase inhibitors; mucolytics; multiple sclerosis medications; muscle relaxants; mydriatics; narcotic antagonists; NMDA receptor antagonists; oligonucleotides; ophthalmic drugs, oxytocics; peptides, polypeptides; proteins; polysaccharides; progestogens; prostaglandins; protease inhibitors; respiratory stimulants; sedatives; serotonin uptake inhibitors; sex hormones; smoking cessation drugs; smooth muscle relaxants and stimulants; steroids; thrombolytics; tranquilizers; urinary acidifiers; urinary incontinence medications; vasodilators; vasoprotectants; skin protectants and sunscreens, and combinations thereof.

In an embodiment for better results, the modified gellan gums of the present disclosure may be processed using manual or automated processes and systems to form different types of scaffolds, such as hydrogels, porous scaffolds, fibres, three-dimensional structures, microparticles, nanoparticles, capsules, membranes, nets, gauzes or disks. In another preferred embodiment, the modified gellan gums may be processed to form sprayable gels with improved mucoadhesive properties.

In an embodiment for better results, the modified gellan gums hydrogels of the present disclosure may further comprise a second modified or non-modified gellan gum.

In an embodiment for better results, the modified gellan gum hydrogels disclosed herein may be used as standalone medical devices as tissue fillers or patches. In a preferred embodiment and by means of example, the modified gellan gum hydrogels may be used as improved medical devices over other materials used for scaffold augmentation in the context of microfracture (MFX). The MFX developed in the 1980's has since become a first-line arthroscopic treatment method for relatively small, symptomatic chondral cartilage lesions. In short, during microfracture, penetration of the subchondral bone plate within the cartilage defect, either by drilling or use of Kirschner wire causes bleeding and formation of a fibrin clot, supposed to fill the defect site and covering the exposed bone surface. Multipotent, bone marrow-derived mesenchymal stem cells then infiltrate into the clot and promote the formation of repair tissue. Unfortunately, the repair tissue consists mainly of fibrocartilaginous cartilage, possessing inferior biochemical and biomechanical properties compared to normal, healthy hyaline-type cartilage. Furthermore, clinical efficacy of the procedure is highly variable, probably due to the fact that the fibrin clot may simply detach from the lesion site, taking with it or allowing escape of the released bone marrow stem cells.

Accordingly, efforts have concentrated on improving the more effective regeneration of hyaline-like tissue by providing an environment within the lesion site more likely to promote increased formation of collagen type II and proteoglycan content. Thus scaffold implants based on natural or synthetic polymers have been proposed for use as medical devices (Table 1) to augment the MFX procedure, with the goal of maintaining the fibrin clot within the defect, facilitating bone marrow stem cell adhesion and migration, whilst assisting integration of repair tissue with the adjacent surrounding area of healthy cartilage.

TABLE I

Scaffold Augmentation Medical Devices in Microfracture

| Relevant Criteria | Gelrin C * Regentis | BST-CarGel ® Piramal | MaloRegen Finceramica | Cellcotec | Chondro-Glde Geistlich | |
|---|---|---|---|---|---|---|
| Classification | Class III Medical device | Class III Medical device | Class III Medical device | Class III Medical device | Class III Medical device | Class III Medical device |
| Physical form | Hydrogel (PEG + fibrinogen) | Hydrogel (chitosan) | Membrane (collagen I/HA) | Scaffold (PEO/PBT) | Membrane (collagen I/III) | Membrane (collagen I/III) |
| Purpose | Cartilage Repair | Cartilage Repair | Cartilage Repair | Cartilage Repair | Cartilage Repair | Cartilage Repair |
| Additional fixation | Yes | No | Yes, Fibrin glue | n/a | Yes, Fibrin glue | Yes |
| Animal component | Yes | Yes | Yes | No | Yes | Yes |
| Application method | microfracture | Arthroscopy microfracture | microfracture | microfracture | Arthrotomy microfracture | ACI |

Notwithstanding, all of the medical devices presented in Table 1 display various disadvantages. Firstly, the latter three require an arthrotomy surgical procedure involving complete exposure of the articular joint, causing patient morbidity and complicated post-surgery recovery process. The ideal medical device should be delivered by a minimally invasive procedure, namely by injection via an arthroscopic procedure. Secondly, the vast majority of existing medical devices in the MFX space contain animal components, which are undesirable due to possible prion contamination and infection issues, allergic reactions as well as ethical considerations in some regions. The ideal medical device would be xeno-free and be manufactured from materials from non-animal sources. Finally, and most importantly, the vast majority of the existing medical devices have no autonomous adhesive properties, meaning that additional fixation aids such as fibrin glue are required. Besides non-xeno-free considerations, this adds another step of complexity to the surgical procedure. The ideal medical device would be able to remain in place within the lesion site without the requirement for further fixation.

Surprisingly, the xeno-free, modified gellan gums herein disclosed present these requirements and overcome the limitations of the current state of the art. Immediately after bleeding is observed during the MFX procedure, the modified gellan gum formulation may be applied to the lesion site via injection by syringe during arthroscopy, and allowed approximately 10 minutes to polymerize. During this time, the modified gellan gum hydrogel is maintained hydrated using 0.9% w/V sodium chloride solution, the monovalent sodium ions of which promote ionic crosslinking of the polymer at the surface. Due to the adhesive properties of the modified gellan gum hydrogels, no further fixation aids are required and the hydrogels are capable of providing a better fill of the lesion site and also maintaining the blood clot containing the bone marrow stem cells within the lesion, leading to regeneration of a higher quality of cartilage and greater integration with surrounding healthy tissue.

In another preferred embodiment, the modified gellan gum hydrogels may be used to encapsulate autologous bone marrow aspirate concentrate, which may be obtained by techniques known to those skilled in the art, and the preparation delivered arthroscopically to the lesion site using the same procedure.

In a further embodiment, the modified gellan gum hydrogels, either alone or with cells, may be further loaded with growth factors, such as, for example, TGF-β1, bone morphogenetic protein-2 (BMP-2), BMP-7 (also known as osteogenic protein-1 [OP-1]) and cartilage-derived morphogenetic proteins CDMP-1 and CDMP-2, platelet lysates and/or small molecules such as antibiotics.

BRIEF DESCRIPTION OF THE DRAWINGS

The following figures provide preferred embodiments for illustrating the description and should not be seen as limiting the scope of invention.

DETAILED DESCRIPTION

The present disclosure provides modified gellan gums containing ion-chelating phenolic and catecholic substituents appropriate to confer improved gelation and formulation characteristics at room and physiological temperature (37° C.), and which form minimally coloured, remarkably surface-adhesive hydrogels which maintain higher cell viability for longer times after encapsulation within the hydrogel and promote up-regulation of the expression of healthy extracellular matrix markers.

One skilled in the art would understand the following description, as well as terminology used herein, as to best describe the disclosed subject matter, and embodiments chosen to do so are not intended to be exhaustive or to limit the invention to the form disclosed. Alternative approaches, equivalents and conditions will be obvious to those skilled in the art.

Purification of Commercial Gellan Gum

Figure 1:
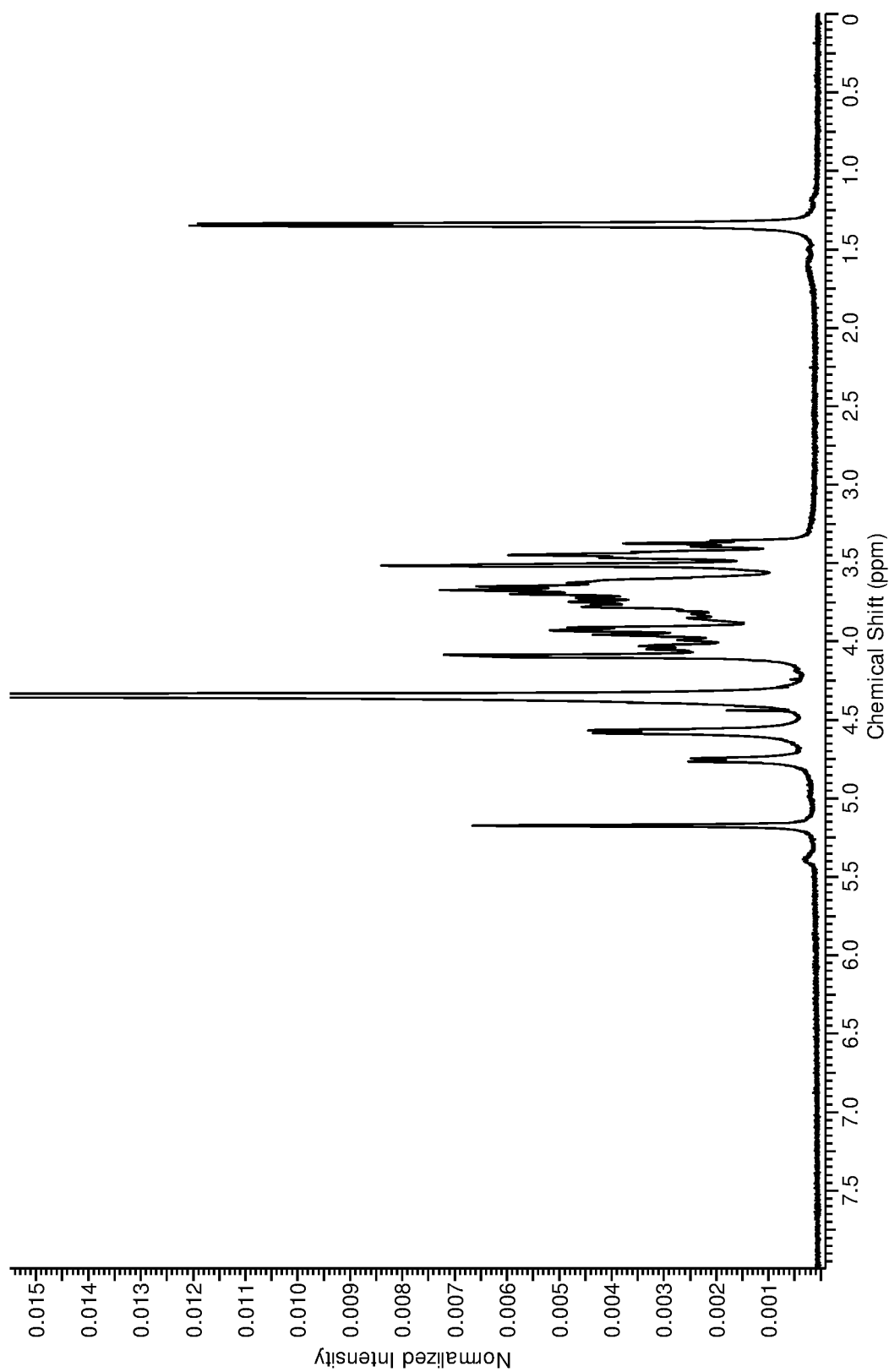
FIG. 1 represents the $^1$H NMR spectrum of purified gellan gum ($D_2O$, 1% w/V, 70° C.).

Commercial gellan gum (Sigma, 5 g) was dissolved in distilled water (500 mL) with heating to 60° C. Amberlyst IR-120 ($H^+$ form) ion exchange resin was added during 30 minutes until the solution pH stabilized at approximately 2.4. The solution was allowed to stir at 60° C. for ten minutes then filtered to remove the resin. To the filtrate was added aqueous sodium hydroxide solution until pH reached 8.5. The solution was poured onto ethanol, forming a precipitate. After stirring at room temperature for one hour, the liquid phase was decanted off and the remaining precipitate was filtered, dissolved in distilled water and dialysed against distilled water. After freezing and freeze-drying, the purified gellan gum was obtained as a white solid, 3.2 g. The $^1$H NMR spectrum of the purified gellan gum product (FIG. 1) is in agreement with the expected structure.

Modification of Purified Gellan Gum with Three Equivalents of Dopamine (GGp-DOPA3)

Figure 2:
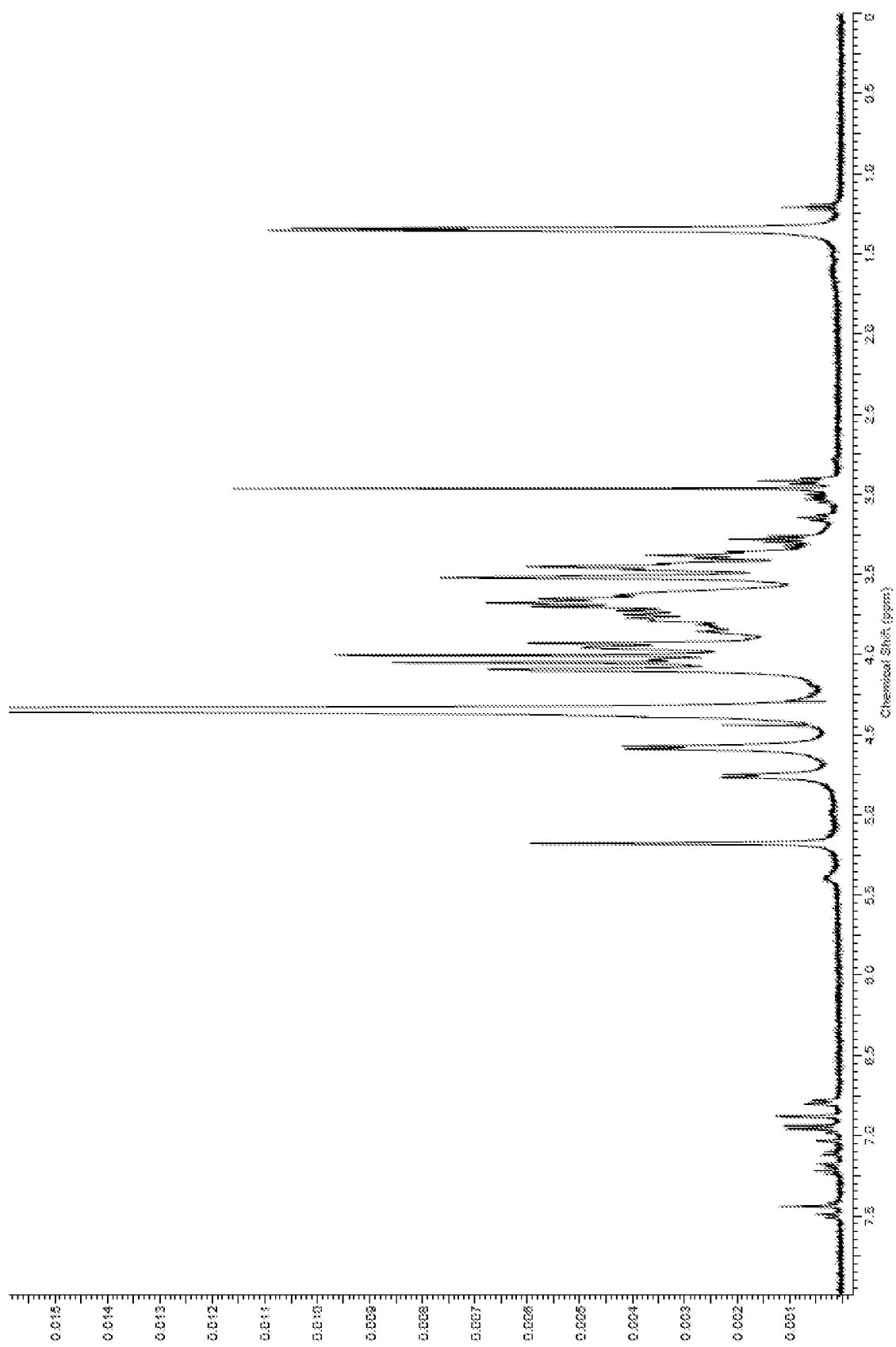
FIG. 2 represents the $^1$H NMR spectrum of purified gellan gum modified with 3 equivalents of dopamine (GG-DOPA3, $D_2O$, 1% w/V, 70° C.).

100 mg of purified gellan gum was dissolved in 10 mL of distilled water at room temperature. Then 0.124 g of DTMMCl were dissolved in 2 mL of water and added dropwise to the solution, which was left to stir for 30 minutes at room temperature. Next, three molar equivalents of dopamine hydrochloride (DOPA, 85 mg) was dissolved in 2 mL of water and added dropwise to the solution and the solution was then left to stir for 24 hours. Next day, the solution was removed from stirring and 10 mL of ethanol were added and the solution was left to rest for 1 hour. Then, the ethanol was decanted and the remaining precipitate was dissolved in distilled water and dialysed against distilled water for 5 days, then frozen at −20° C. and freeze-dried to give the product (GGp-DOPA3) as a white solid 128 mg. The $^1$H NMR spectrum of the product (FIG. 2) is in agreement with the expected structure of gellan gum modified by dopamine. The degree of substitution in this case was determined as approximately 4%.

By appropriately decreasing or increasing the molar equivalents of activating agent and dopamine hydrochloride used in the above example relative to the purified gellan gum starting material, it is possible to obtain modified gellan gums with degrees of substitution in the range 0.01-30%. For example, applying the procedure described above with either 1 or 7.5 molar equivalents, it is possible to obtain DOPA-modified gellan gum with lower (GGp-DOPA1) and higher (GGp-DOPA7.5) degrees of substitution (2.1 and 5.6%), respectively.

Typically the DOPA-modified gellan gums contain approximately 7-10% residual moisture in the form of water. Tests for residual solvents, metals, heavy metals and leachable impurities return analytical levels normally below the detection limit of the test method.

By further varying the molecular weight of the purified gellan gum starting material, it is possible to obtain DOPA-modified gellan gums with various molecular weights (Table II), as determined by gel-permeation or size-exclusion chromatography (GPC-SEC), a standard technique for determining average molecular weight (Mw), average molecular number (Mn) and intrinsic viscosity (IV) of polymeric materials.

TABLE II

Molecular weight of representative batches of GGp-DOPA3 using purified gellan gum starting material with different molecular weight.

| Batch | Mw (KDa) | Mn (KDa) | Mw/Mn | IV (cm$^3$/g) |
|---|---|---|---|---|
| #1 | 2080 | 1170 | 1.8 | 3190 |
| #2 | 1454 | 673 | 2.2 | 2020 |
| #3 | 2604 | 1687 | 1.5 | 4247 |

As will be obvious to those skilled in the art, by application of the same synthetic procedure and employing appropriately substituted alcohols (R7-OH) and primary/secondary amines (HN—R7R8) instead of dopamine, the full range of modified gellan gums disclosed herein may be prepared.

Nitration of Dopamine Hydrochloride

Figure 3:
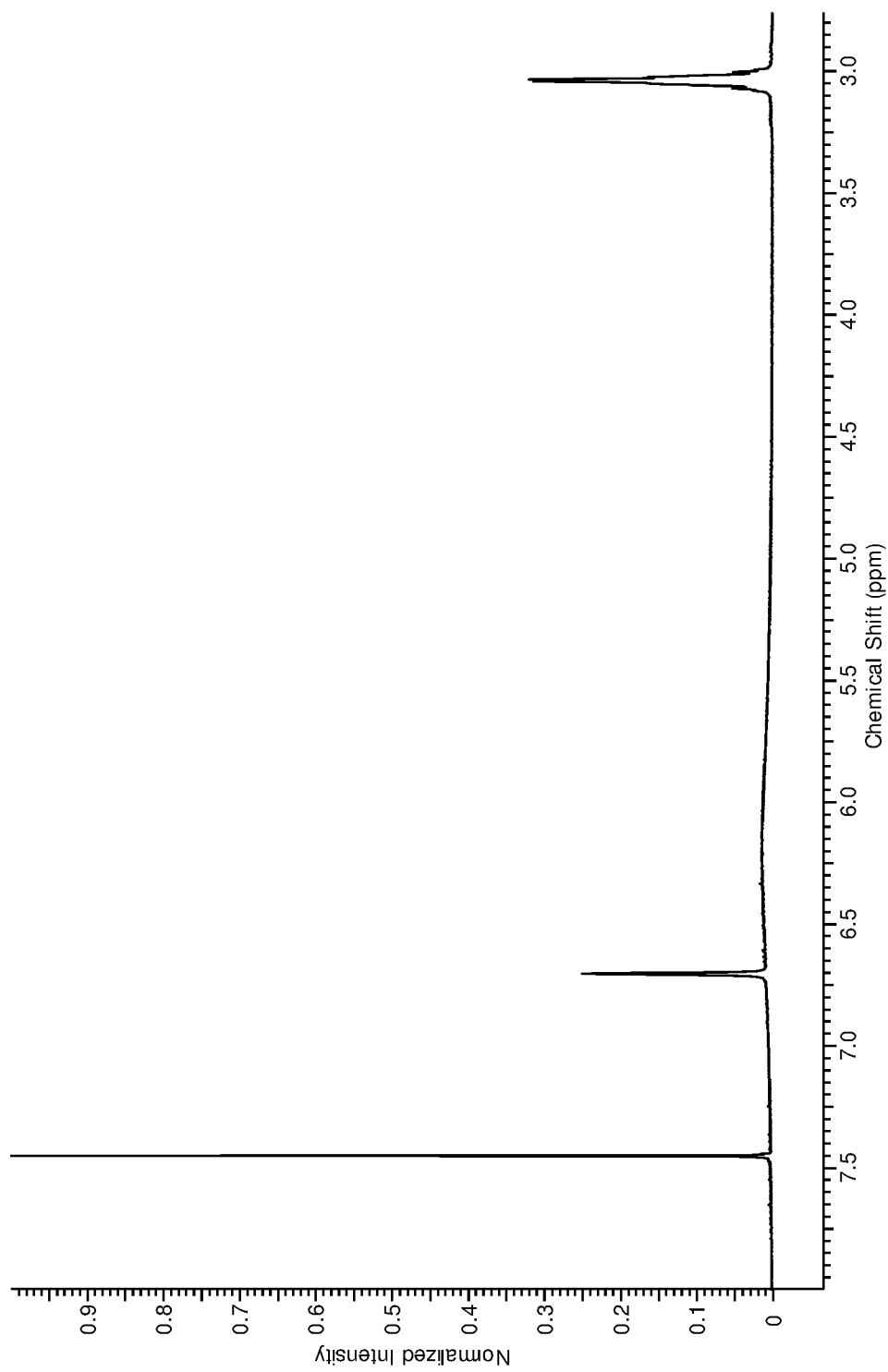
FIG. 3 represents the $^1$H NMR spectrum of 6-nitrodopamine hemisulphate (NITRODOPA, DMSO-d6, 1% w/V, 70° C.).

To a stirred solution of dopamine hydrochloride (1.92 g, 10 mmol) in distilled water (25 mL) was added sodium nitrite (1.52 g, 22 mmol) and the solution was cooled in an ice-water bath. Thereupon, a solution of sulphuric acid (1 mL) in distilled water (10 mL) was added dropwise causing the reaction mixture to turn deep orange-red in appearance. Towards the end of addition, a thick yellow-orange precipitate formed. The mixture was then allowed to stir at room temperature overnight, then filtered and washed sequentially with ice-cold water, absolute ethanol and then diethyl ether. After drying under vacuum, 6-nitrodopamine hemisulphate was obtained as a yellow solid. The $^1$H NMR spectrum of the product (FIG. 3) is in agreement with the expected structure.

Modification of Purified Gellan Gum with One Equivalent of 6-nitrodopamine (GGp-NITRODOPA1)

Figure 4:
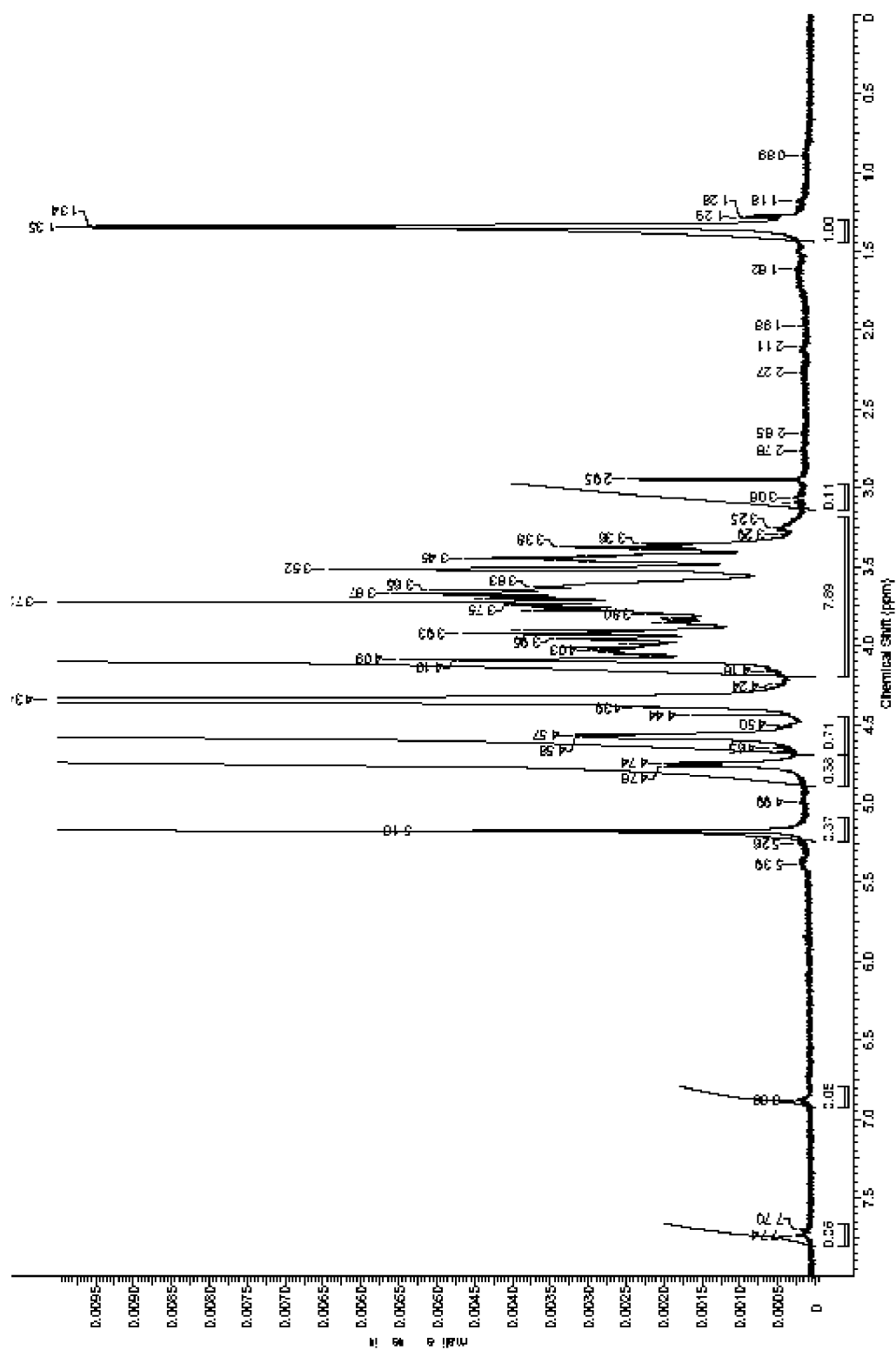
FIG. 4 represents the $^1$H NMR spectrum of purified gellan gum modified with 1 equivalents of 6-nitrodopamine (GG-NITRODOPA1, $D_2O$, 1% w/V, 70° C.).

500 mg of purified gellan gum was dissolved in distilled water (50 mL) at room temperature. Then 0.20 g of DTMMCI were dissolved in distilled water (5 mL) and added dropwise to the solution which was left to stir for 30 minutes at room temperature. Next, one molar equivalent of 6-nitrodopamine hemisulphate (NITRODOPA, 220 mg) was dissolved in N,N-dimethylacetamide (8 mL) and added dropwise to the solution which was then left to stir for 24 hours. Next day, the solution was poured onto 500 mL of ethanol and the precipitate was left stirring for 1 hour. Then, the precipitate was filtered off, washed with ethanol, and then dissolved in distilled water (200 mL). The product was dialysed against distilled water for 5 days, then frozen and freeze-dried to give the product (GGp-NITRODOPA1) as an orange-yellowish solid. The $^1$H NMR spectrum (FIG. 4) of the product is in agreement with the expected structure of gellan gum modified by nitrodopamine.

By appropriately decreasing or increasing the molar equivalents of activating agent and nitrodopamine hemisulphate used in the above example, it is possible to obtain modified gellan gums with degrees of substitution in the range 0.01-30%. For example, applying the procedure described above with either 3 molar equivalents, it is possible to obtain NITRODOPA-modified gellan gum with higher (GGp-NITRODOPA3) degrees of substitution.

2-Chlorodopamine hydrochloride (McCarthy, 1986) and 1-(2'-aminoethyl)-2-methyl-3-hydroxy-4-pyridinone dihydrochloride (Dobbin, 1993) were prepared as described. By application of the procedure of the above described example with these materials, the corresponding modified gellan gum hydrogel precursors were also obtained.

In a preferred embodiment, the modified gellan gums, herein exemplified by GG-DOPA3, may be dissolved and maintained in deionized water, sterile or otherwise, at temperatures between 5 and 40° C., preferably between 15 and 37° C., preferably under mild agitation in less than one hour. Also in another preferred embodiment, the dissolution media may comprise cell culture media, phosphate buffer saline solution or sodium chloride saline solution.

In one embodiment, the dissolution time is between 0.5 and 1 hour, preferably in less than thirty minutes.

Preferred concentrations of the modified gellan gum solutions are between 0.01% and 5% w/V, more preferably between 0.1 and 4% w/V and even more preferably between 0.5 and 3% w/V.

Figure 5:
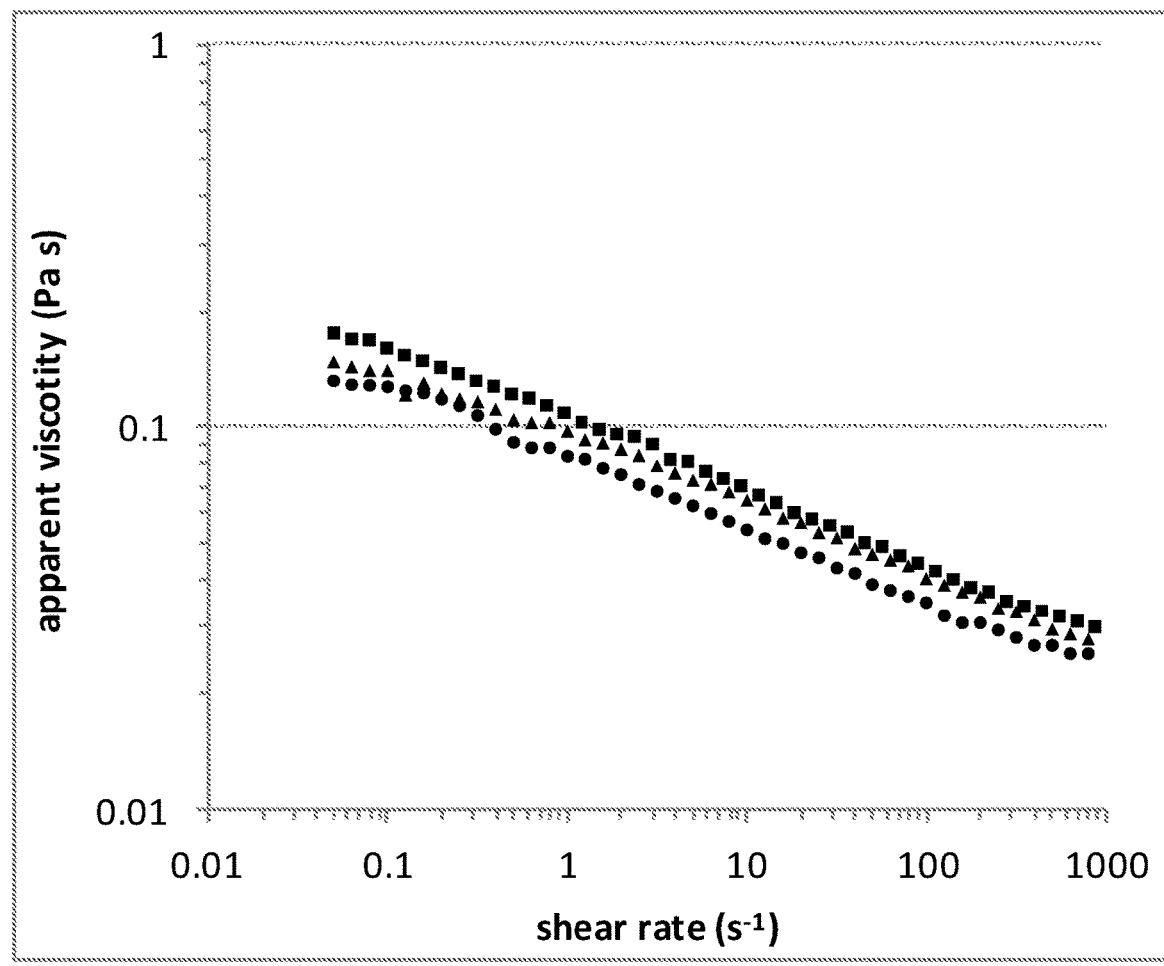
FIG. 5 represents the viscosity profile as a function of increasing shear rate of a solution of GG-DOPA3 in water at a concentration of 1% w/V.

In a preferred embodiment, modified gellan gum solutions are shear-thinning liquids which (FIG. 5) that are sufficiently mobile and have suitable viscosity as to be injected by syringe. Preferred intrinsic viscosities for modified gellan gum solutions are in the range of 1000-5000 cm$^3$/g, more preferably 1500-4500 cm$^3$/g at a concentration of 5 mg/mL (Table II). Modified gellan gum solutions are considerably free of entrapped air and are transparent and colourless, practically colourless or lowly coloured in appearance. Modified gellan gum hydrogels formed by ionic crosslinking of such solutions are transparent and significantly free of entrapped air bubbles.

Modified Gellan Gum Hydrogel Formation

Initial target polymer concentration is 1.25% w/V. Weigh 12.5 mg of GGp-DOPA3 into a plastic vial and add a magnetic stirring bar. Add 1 mL of sterile water for injection. Manually and gently, make sure that the water in the vial contacts all the material for moistening. Begin magnetic stirring and continue until the material is completely dissolved at room temperature. The final solution is transparent and viscous. The formation of bubbles is minimised using ideal magnet dimensions and magnetic stirring rate indicated. If required, rest the solution to allow entrapped air bubbles to escape.

Figure 6:
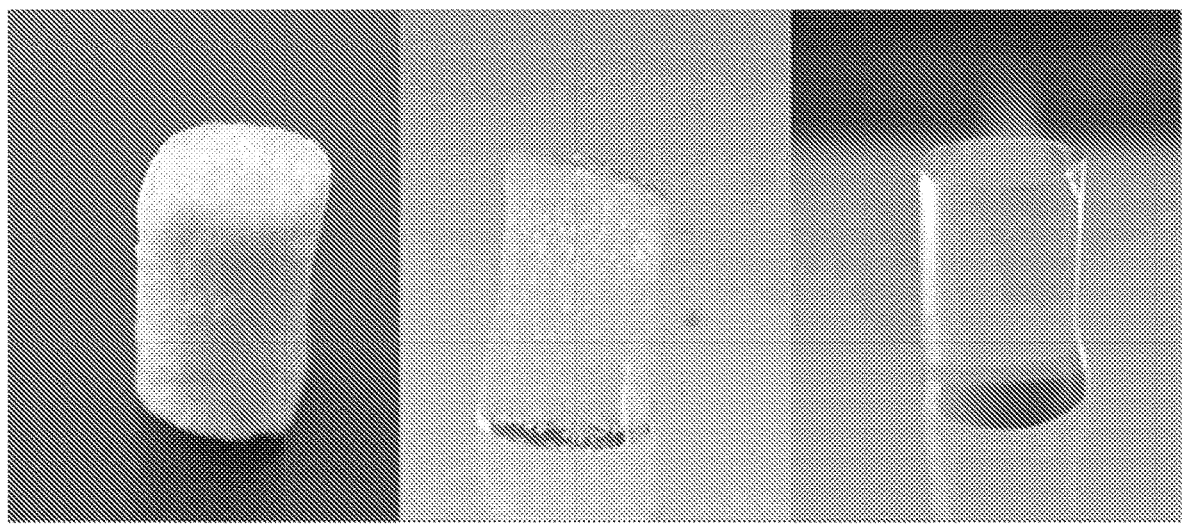
FIG. 6 represents a typical porous dehydrated acellular scaffold (left), rehydrated acellular scaffold (middle), and hydrogel (right) prepared from the modified gellan gums.

After dissolution is complete, stop magnetic stirring. Add 250 μL of phosphate buffered saline (PBS with $Ca^{2+}/Mg^{2+}$) to the polymer solution (8:2 ratio of hydrogel:PBS with $Ca^{2+}/Mg^{2+}$). The divalent cations in the PBS with $Ca^{2+}/Mg^{2+}$ promote ionic crosslinking of the polymer. Final polymer concentration is 1% w/V. Gently swirl the solution for one minute. Meanwhile, in well plates, place a cylindrical plastic mold in the bottom of each well. Carefully fill the molds with the desired volume of crosslinked polymer solution without disturbing the mold. After 5 minutes, cover the mold with PBS (with $Ca^{2+}/Mg^{2+}$). Let the well plate rest for an appropriate time, then remove the molds. Leave the gels resting in the PBS solution (in suspension) for an appropriate time. Remove the gels from the well plates (FIG. 6, right).

In another preferred embodiment, cell culture medium can be used instead of PBS to promote ionic-crosslinking.

In a further preferred embodiment, cations other than $Ca^{2+}$ and $Mg^{2+}$ can be added to form modified gellan gum hydrogels via ionic cross-linking. One or more divalent and trivalent ions, or mixtures thereof, such as $Fe^{2+}$, $Cu^{2+}$, $Sr^{2+}$, $Ba^{2+}$, $Co^{2+}$, $Mn^{2+}$, $Ni^{2+}$, $Sn^{2+}$, $Zn^{2+}$, $Fe^{3+}$, $Al^{3+}$, $Ga^{3+}$ and $Ti^{3+}$ may be added to the preparation in pharmaceutically acceptable salt form, such as chlorides and sulphates and hydrates thereof, at physiologically relevant concentrations. Due to the different valency and ionic radii of these ions, modified gellan gum hydrogels with a wide range of physiochemical and mechanical properties can be obtained.

Surprisingly, in contrast to gellan gum and previously reported modifications of gellan gum, ions other than divalent and trivalent cations may be used to ionically crosslink the modified gellan gums herein disclosed at equivalent concentrations. In particular, physiologically relevant monovalent cations such as $Na^+$, $K^+$ and $Li^+$ alone or mixtures thereof, are all able to promote formation of mechanically stable hydrogels. This is in contrast to unmodified purified gellan gum, which as mentioned earlier, does not form hydrogels in the presence of monovalent cations only. In a preferred embodiment, ionic crosslinking is promoted by 0.9% sodium chloride solution.

Figure 7:
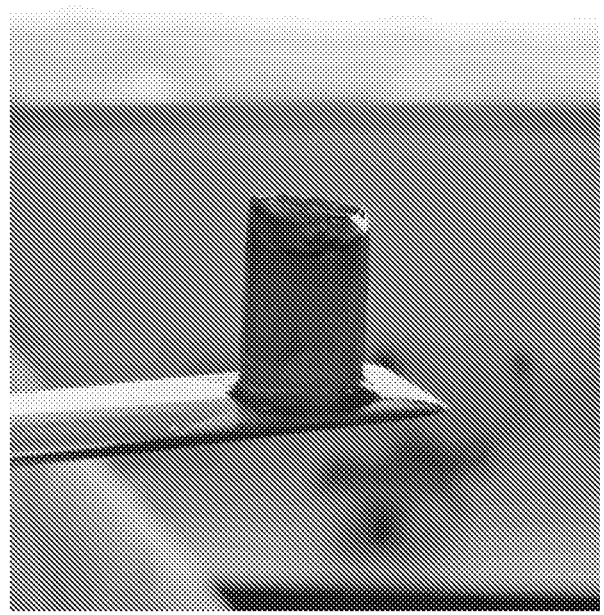
FIG. 7 represents a typical hydrogel prepared from a modified gellan gum using whole blood as crosslinker.

This finding is particularly relevant with respect to physiological fluids. Thus, modified gellan gum hydrogels may be obtained by using human or animal whole blood or plasma as crosslinking agent (FIG. 7) since these are rich in monovalent cations as electrolytes. This aspect is of particular relevance within the context of microfracture.

Furthermore, the surprising ability of the modified gellan gums disclosed herein to form stable hydrogels in the presence of monovalent cations overcomes the mechanical stability issues observed over time in vivo with gellan gum and methacrylated gum, related to the exchange of divalent and monovalent cations. Thus the modified gellan gums disclosed herein are able to maintain their mechanical properties over a longer period in vivo than both gellan gum and methacrylated gellan gum.

Modified Gellan Gum Porous Acellular Scaffolds

Modified gellan gum porous acellular scaffolds may be formed from the modified gellan gums by applying the following representative procedure.

GGp-DOPA3 (375 mg) was dissolved in distilled water (30 mL) at room temperature under stirring to give a 1.25% w/V solution. Then, 7.5 mL of PBS containing $Ca^{2+}$ and $Mg^{2+}$ ions was placed at the centre of a plastic disc and immediately after, the GGp-DOPA3 solution was added to the plastic disk and vigorously mixed with the crosslinking solution by use of a spatula. The resulting mixture was then left to stand for thirty minutes to one hour. After this period, further PBS solution was added until the top of the disc was completely submersed. The disc was then allowed to rest for fifteen to thirty minutes. Polymeric cylinders were then formed by punching the hydrogel with a cylindrical punch having 12 mm diameter. The resulting polymeric cylinders were then transferred to 24 well plates (one disc in each well) and covered with PBS, and then changing the PBS every 9 hours three times. Then, after removing the excess PBS from each well, the plates were frozen at −80° C. for twenty-four hours. The plates are then removed from the freezer and lyophilized for three to five days to give the porous dehydrated GGp-DOPA3 scaffold (FIG. 6, left).

Said porous scaffolds may be use used as tissue implants, tissue fillers or for scaffold augmentation for example in conjunction with microfracture.

The GGp-DOPA3 scaffolds may be rehydrated using for example PBS solution (FIG. 6, middle) and used as such as acellular constructs, or may be used for in vitro seeding of various cell types including adipose or bone-marrow derived mesenchymal stromal/stem cells, thereby providing cell-laden implants for in vivo applications.

Swelling Characteristics of GGp-DOPA3 Scaffolds

Figure 8:
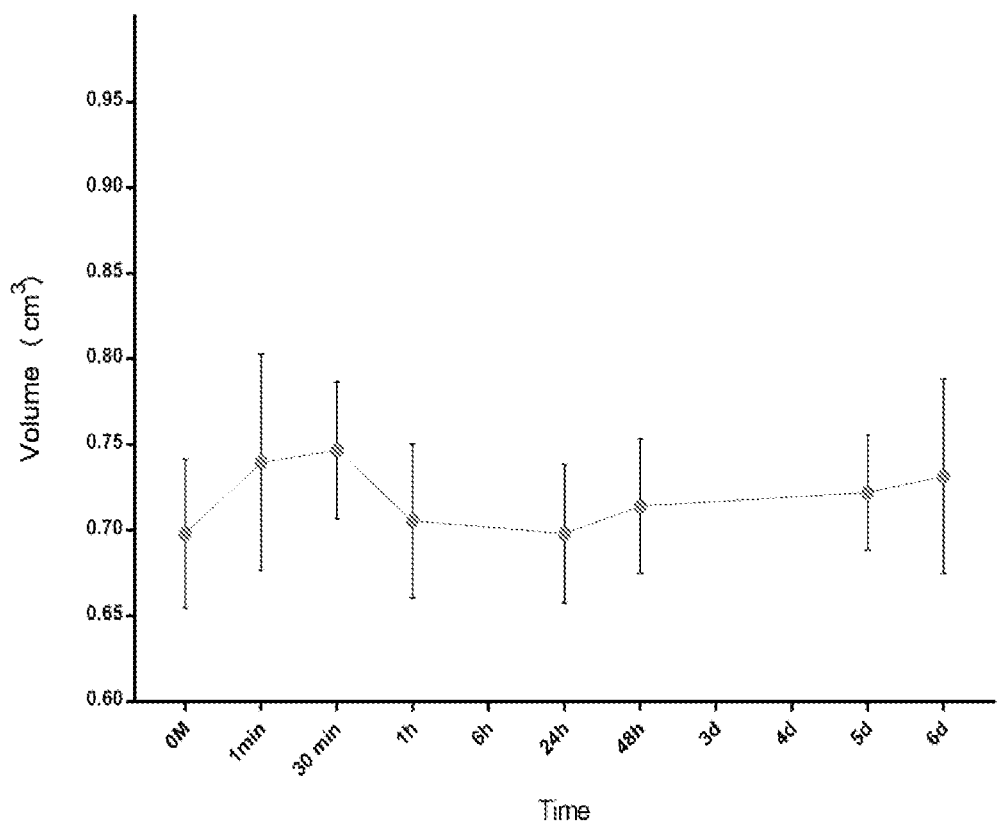
FIG. 8 represents the swelling characteristics of modified gellan gum scaffolds immersed in aqueous solution over time.

Nine cylindrical scaffolds were measured (length and height) with a caliper and each scaffold was placed in a separate plate well. Each well was filled with PBS and, after 1 minute, the scaffolds were removed from the solution and immediately measured (length and height) with a caliper. Afterwards, the scaffolds were immediately placed again in the PBS solution, and the same procedure was repeated at time points of 30 minutes, 1 hour, 6 hours, 24 hours, 2 days, 3 days, 4 days, 5 days and 6 days. All the measurements were recorded, and the volume of the scaffolds at different time points was calculated as shown in FIG. 8.

Water-Uptake Characteristics of GGp-DOPA3 Scaffolds

Figure 9:
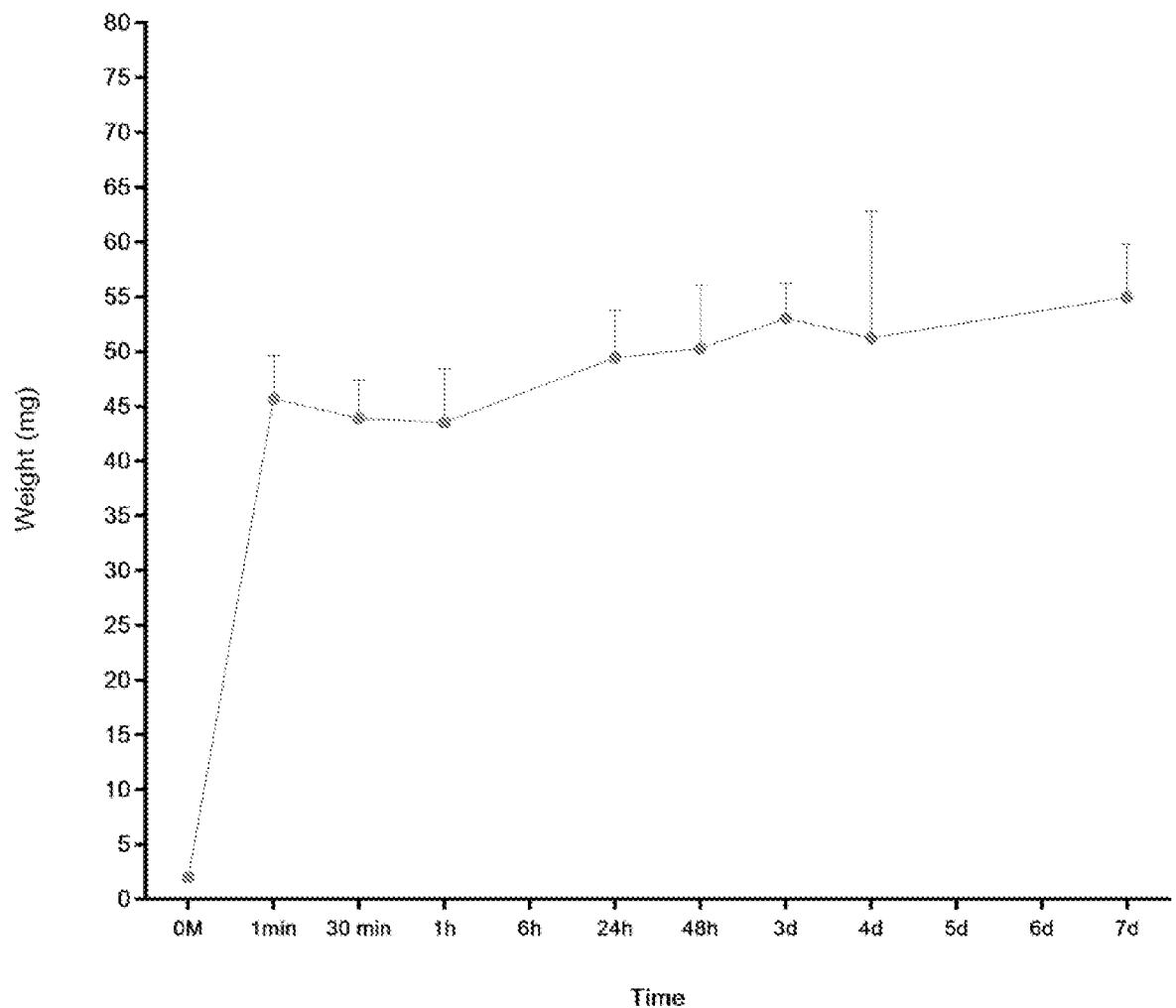
FIG. 9 represents the water-uptake capacity of modified gellan gum scaffolds immersed in aqueous solution over time.

Nine cylindrical scaffolds were weighed and each scaffold was placed in a separate plate well. Each well was filled with PBS. After 1 minute, the scaffolds were removed from the solution and the excessive solution was removed and the scaffolds were weighed. Afterwards, the scaffolds were placed again in the solution, and the same procedure was repeated at time points of 30 minutes, 1 hour, 6 hours, 24 hours, 2 days, 3 days, 4 days, 5 days and 6 days. All the weights were recorded at the different time point as shown in FIG. 9.

Evaluation and Comparison of GGp-DOPA Hydrogel Adhesiveness—Fixation within a Chondral Lesion—Ex Vivo In the human knee joint, the medial femoral chondyle is the most frequent site of deep grade III and IV lesions. Human lesions treated for cartilage repair vary from 0.5-12 $cm^2$ in size. In humans, the average articular cartilage thickness over 5 locations ranges from 2.2-2.5 mm, compared to 2-4 mm in pigs. With respect to cartilage thickness for induction of chondral lesions, the porcine model better resembles the scenario in humans. Thus, ex vivo conditions similar to those found in humans were used to test fixation of the new modified gellan gum-based hydrogels, including: lesion location, size, depth as well as physical stress (gravity and friction).

Circular 8 mm diameter (0.5 $cm^2$) chondral lesions were created in an articular porcine joint (critical size defect—50% of chondyle width). The cartilage in the lesion site was removed until the subchondral bone was reached and the depth of the lesions was approximately 2 mm. The defined hydrogel volume to perform the test was calculated for each lesion ($V=\pi r^2 \times height$). GGp-DOPA1 (1% w/V), GGp-DOPA3 (1% w/V), GGp (1% w/V) and GG-MA (2% w/V) hydrogels were formulated as previously described and pipetted into the lesions, so that each lesion was completely filled. Physiological saline solution (0.9% w/V) was then used to induce crosslinking for 5 minutes. The following stress tests were performed;

Gravity test: The prototype was slowly rotated upside-down, placing the lesion faced down. The prototype was vigorously shaken in order to confirm fixation of the hydrogel within the lesion (positive result) or if hydrogel dislocates from lesion (negative result).

Friction test—The prototype joint was assembled and articular motion mimicked in order to confirm hydrogel fixation within the lesion (positive result) or if hydrogel breaks or dislocates from lesion (negative result).

Fixation within physiological temperature was further mimicked by immersing the articular joint in 37° C. saline solution overnight.

Figure 10A:
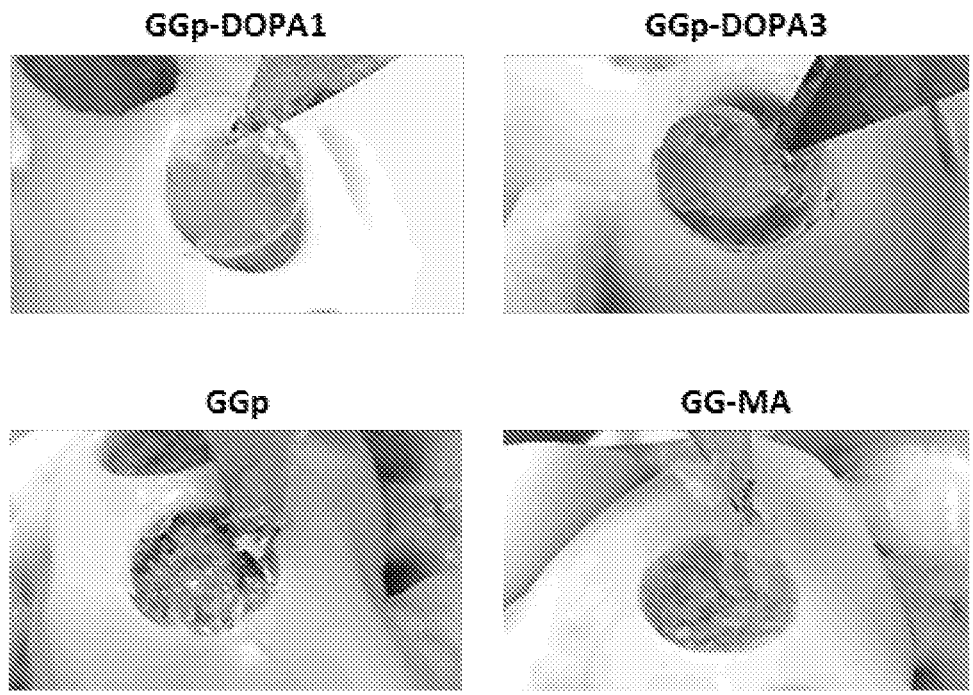
FIG. 10a represents the fixation of GG-based hydrogels within ex vivo chondral lesions of 8 mm diameter and 2 mm thick, after testing conditions. Note complete fixation of GGp-DOPA1 and GGp-DOPA3 hydrogels and only partial fixation of GGp and GG-MA hydrogels.

Both GGp-DOPA hydrogel formulations (GGp-DOPA1 and GGp-DOPA3) successfully withstood all stress test conditions, maintaining full integrity within chondral lesions of 2 mm thickness (FIG. 10a). In addition, it was possible to remove the 3D GGp-DOPA hydrogels fully intact from the lesion after fixation tests. On the contrary, only partial fixation of GGp and GG-MA formulations was observed within the same testing system, and hydrogel fragmentation was also observed.

Regarding the concentration of hydrogel formulations, 1% w/V was found to be particularly suitable for GGp-DOPA1, GGp-DOPA3 and GGp with respect to powder dissolution time, solution viscosity and 3D hydrogel consistency and stability. For GG-MA however, a minimal concentration of 2% w/V was required to achieve similar properties. These results confirm significantly greater adhesiveness of gellan gum hydrogels modified with ion-chelating substituents at equal or lower concentrations than state of the art gellan gum hydrogels.

Figure 10B:
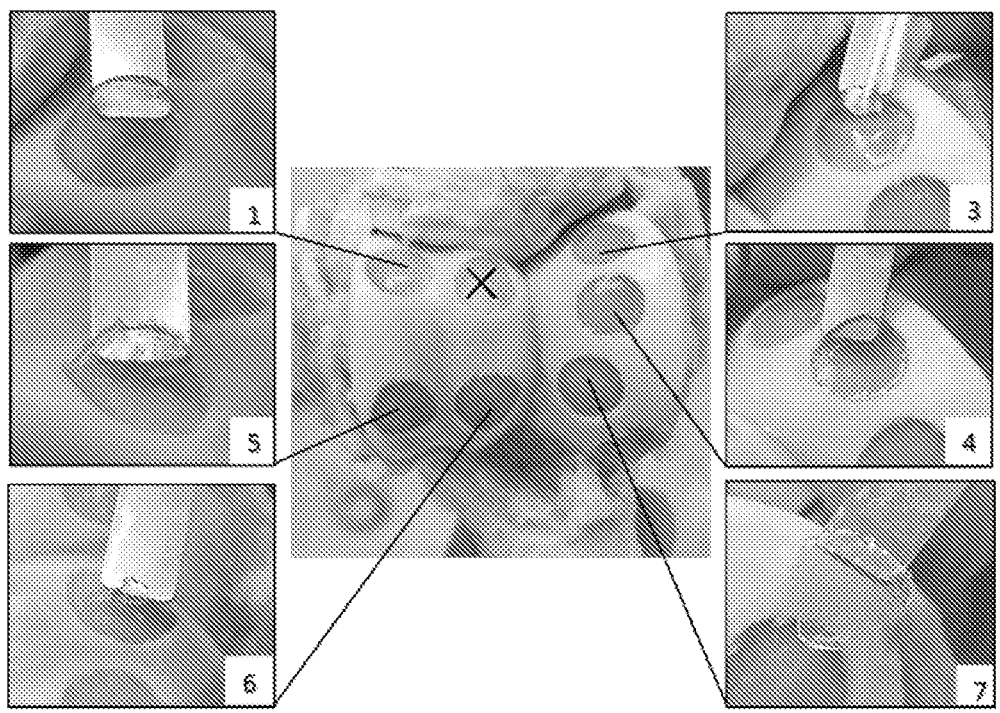
FIG. 10b represents a porcine joint (center image) with the six defects shown as 1 and 3-7 filled with GGp-DOPA3 hydrogels after passing all the adhesive tests in sequence. The defect shown as X is the empty control lesion.

In order to further confirm the adhesive properties of the gellan gum hydrogels, this fixation test was repeated with cartilage lesions created in several positions within a porcine joint, wherein variations in cartilage thickness could further challenge adhesion of the hydrogel. In all six positions (FIG. 10b), the hydrogel was found in place after the sequence of tests.

The improved adhesive properties of the modified gellan gum hydrogels herein disclosed mean that cartilage lesions of greater size may be treated (>4 $cm^2$), since unlike other hydrogels, the present modified gellan gum hydrogels are able to stick to surfaces of greater area. By means of example, currently available treatment options such as microfracture, ACI or MACI are only effective for treating smaller lesions between 1-4 $cm^2$. Thus the modified gellan gum hydrogels offer advantages over current state of the art and standard of care treatment options.

Assessment of Cell Viability within GGp-DOPA Hydrogels In Vitro

Viability of human chondrogenic cells encapsulated within the gellan gum-based hydrogels was assessed by in vitro culture up to 21 days, this being the minimum timeframe needed for chondrogenesis. Cells were mixed with representative GG-based solutions at room temperature, to yield GGp-DOPA1, GGp-DOPA3 and GGp hydrogels at 1% w/V concentration, and GG-MA hydrogels at 2% w/V concentration, all formulations containing 5 million cells/mL.

Two independent cultures with different cell types were performed, namely with human chondrocytes and human adipose mesenchymal stromal/stem cells (hASC). hASC were maintained undifferentiated or induced into the chondrogenic lineage, using chondrogenic growth factors. Individual 20 µL cellular hydrogels were pipetted and cell culture media was added to promote crosslinking of the hydrogels, resulting in stable and transferrable individual 3D structures.

Figure 11:
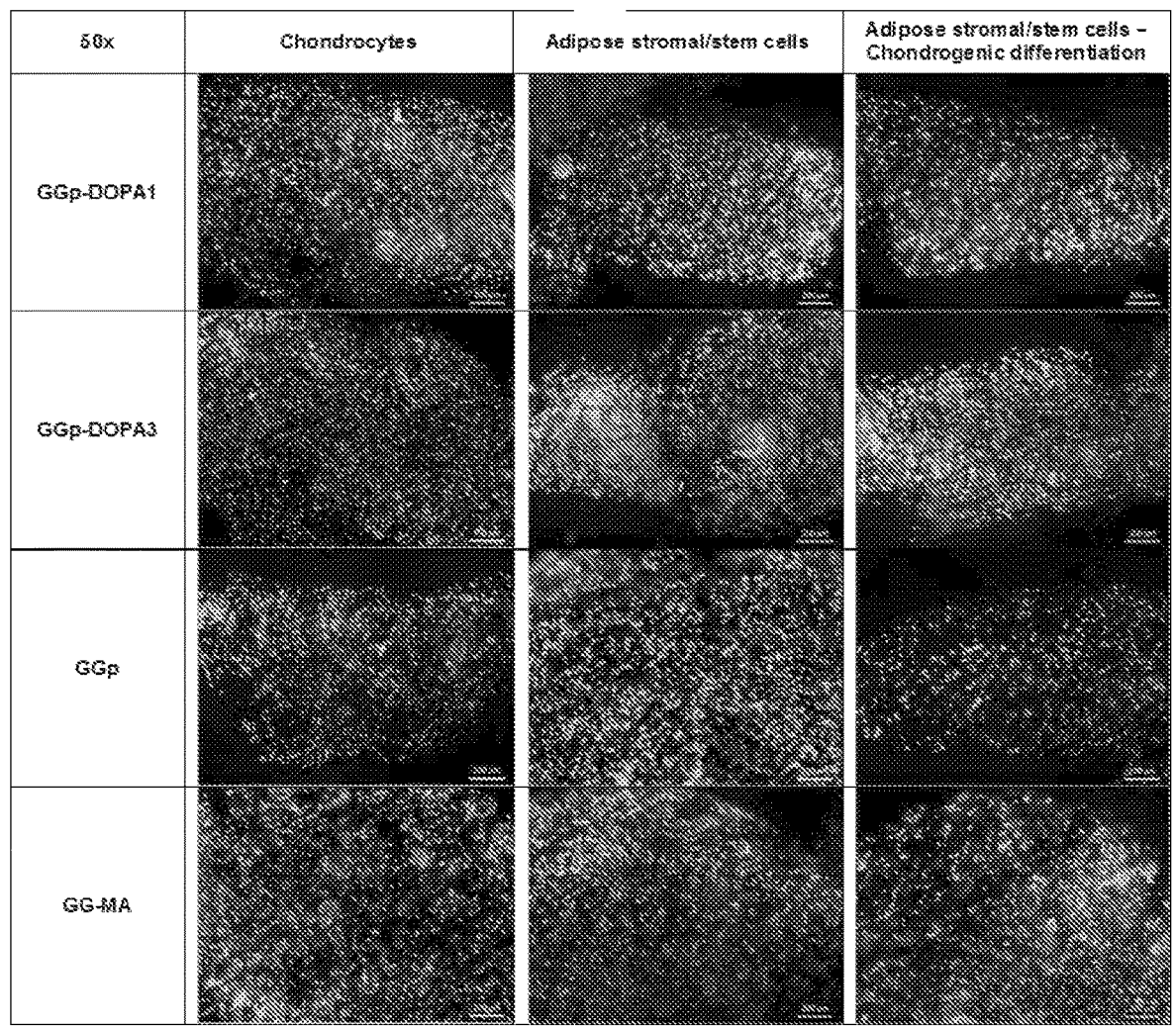
FIG. 11 represents the live/dead imaging of cells encapsulated in GG-based formulations after 21 days of culture. Green=Live; Red=Dead. Magnification=50×.

After in vitro culture, live and dead cells were microscopically observed by specific staining, whereby live cells are stained green by calcein AM, and dead cells are stained red by propidium iodide (FIG. 11).

Regarding adipose stromal/stem cells, clearly increased live cell density is observed within the GGp-DOPA3 hydrogel, as compared to other formulations. This was evident for both differentiated and non-differentiated cells (FIG. 11, middle and right column). In addition, better cell distribution is observed within the GGp-DOPA3 hydrogel than within the GGp-DOPA1 hydrogel, while significantly void zones without cells were observed within the GGp and GG-MA hydrogels.

As for chondrocyte culture, practically equivalent cell density and viability was observed amongst the various hydrogel formulations (FIG. 11, left column). These results confirm that GGp-DOPA hydrogels are able to maintain different cell types viable for long periods after encapsulation compared to state of the art gellan gum hydrogels and that by judicious choice of substitution degree, it is possible to optimize cell viability and distribution through the hydrogel.

Evaluation of Chondrogenesis within GGp-DOPA Hydrogels In Vitro

Collagen type II is the most abundant extracellular matrix component of healthy articular hyaline cartilage. On the other hand, presence of collagen type I is related with an unhealthy, fibrous cartilage tissue.

Therefore, the expression of these two markers by human chondrogenic cells, encapsulated within the gellan gum-based hydrogels was assessed by in vitro culture up to 21 days. The experimental protocol was as described earlier for evaluation of cell viability.

Figure 12:
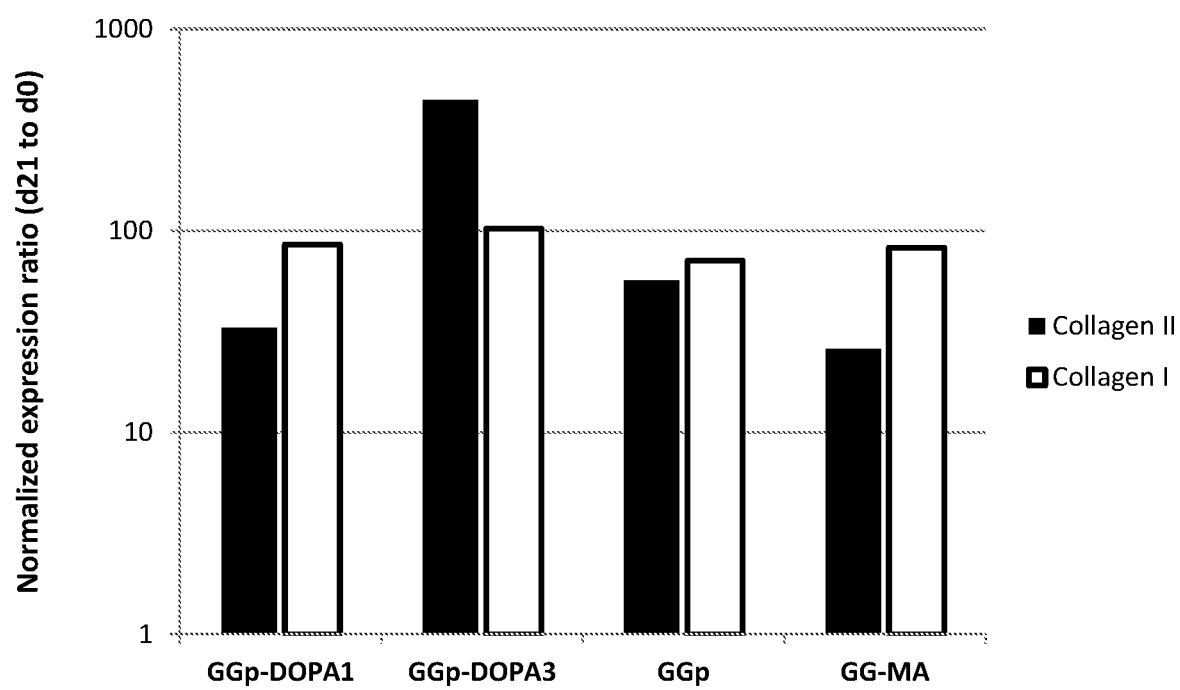
FIG. 12 represents the gene expression of human adipose stromal/stem cells differentiated into chondrogenic lineage within GGp-DOPA1, GGp-DOPA3, GGp or GG-MA hydrogels. Results presented as expression ratio of cells after 21 days of culture (d21), normalized to pre-culture values (d0).

It was surprisingly found that the different hydrogel formulations had a very profound and unexpected impact on the expression of collagen type II and collagen type I. Among the four formulations tested, GGp-DOPA3 clearly induced expression of collagen type II to levels higher than collagen type I (FIG. 12). While this differentiating factor was evident, even more remarkable is the fact that expression of collagen type II was four times higher than collagen type I. In addition to increased expression of collagen II as compared to collagen I, the overall level of collagen type II up-regulation was on average thirteen times higher by GGp-DOPA3 than any of the other formulations, which also upholds its chondrogenic-friendly character.

Thus it is surprisingly shown that both the nature of ion-chelating group and the degree of substitution of gellan gum by this substituent favours chondrogenesis. Considering potential therapeutic applications such as hyaline cartilage regeneration, certain modified gellan gum hydrogels containing ion-chelating groups with defined substitution degree as described herein have the potential to markedly improve efficacy of cell-based cartilage lesion therapeutics.

Accordingly, the gellan gum hydrogels modified with ion-chelating substituents as described herein present significant advantages for in vitro cell culture and for tissue engineering and regenerative medicine by promoting long term cell viability and up-regulation of the expression of healthy extracellular matrix markers, whilst displaying improved adhesive behavior within bodily tissues and surfaces.

The term "comprising" whenever used in this document is intended to indicate the presence of stated features, integers, steps, components, but not to preclude the presence or addition of one or more other features, integers, steps, components or groups thereof.

All references recited in this document are incorporated herein in their entirety by reference, as if each and every reference had been incorporated by reference individually.

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

Where singular forms of elements or features are used in the specification of the claims, the plural form is also included, and vice versa, if not specifically excluded. For example, the term "a cell" or "the cell" also includes the plural forms "cells" or "the cells," and vice versa. In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

The above described embodiments are combinable.

The following claims further set out particular embodiments of the disclosure.

REFERENCES

Oliveira, J. T., Sousa, R. A., Reis, R. L. (2009) Gellan gum based hydrogels for regenerative medicine and tissue engineering applications, its system and processing devices. WO2009/101518 A2.

Oliveira, J. T., Santos, T. C., Martins, I., Picciochi, R., Marques, A. P., Castro A. G., Neves, N. N., Mano, J. F., Reis, R. L. (2010) Gellan gum injectable hydrogels for cartilage tissue engineering applications: In vitro studies and preliminary in vivo evaluation. Tissue Engineering Part A. 16(1): 343-353.

Silva-Correia, J., Oliveira, J. M., Oliveira, J. T., Sousa, R. A., Reis, R. L. (2011a) Photo-crosslinked gellan gum-based hydrogels: preparation methods and uses thereof. WO2011/119059 A1.

Silva-Correia, J., Oliveira, J. M., Caridade, S. G., Oliveira, J. T., Sousa, R. A., Mano, J. F., Reis, R. L. (2011b) Gellan gum hydrogels for intervertebral disc tissue-engineering applications. J. Tissue Eng. Regen. Med., 5, 97-107.

Silva-Correia, J., Zavan, B., Vindigni, V., Silva, T. H., Oliveira, J. M., Abatangelo, G., Reis, R. L. (2013) Biocompatibility evaluation of ionic- and photo-crosslinked methacryalted gellan gum hydrogels: in vitro and in vivo study. Adv. Healthcare Mater., 2, 568-575.

Ryu, J. H., Hong, S., Lee, H. (2015) Bio-inspired adhesive catechol-conjugated chitosan for biomedical applications: a mini-review. Acta Biomaterialia, 27, 101-115.

Lee, C., Shin, J., Lee, J. S., Byun, E., Ryu, J. H., Um, S. H., Kim, D-I., Lee, H., Cho, S-W. (2013) Bioinspired, calcium-free alginate hydrogels with tunable physical and mechanical properties and improved biocompatibility. Biomacromolecules, 14(6), 2004-2013.

Barret, D. G., Fullenkamp, D. E., He, L., Holten-Andersen, N., Lee, K. Y, Messersmith, P. B. (2013) pH-Based regulation of hydrogel mechanical properties through mussel-inspired chemistry and processing. Adv. Funct. Mater., 23, 1111-1119.

Shin, J., Lee, J. S., Lee, C., Park, H-J., Yang, K., Jin, Y., Ryu, J. H., Hong, K. S., Moon, S-H., Chung, H-M. Yang, H. S., Um, S. H., Oh, J-W., Kim, D-I., Lee, H., Cho, S-W. (2015) Tissue adhesive catechol modified hyaluronic acid hydrogel for effective, minimally invasive cell therapy. Adv. Funct. Mater., 25, 3814-3824.

Lee, H., Lee, M., Ryu, H. J. (2013) Hydrogel comprising catechol group-coupled chitosan or polyamine and poloxamer comprising thiol group coupled to end thereof, preparation method thereof, and hemostat using same. AU2011381641 B2.

Manolakis, I., Noordover, J. A., Vendamme, R., Eevers, W. E. (2014) Hydroxyphenyl functionalized poly (ester amide). EP2784101 A1.

Park, K-D., Joung, Y-K., Park, K-M., Lih, E-G. (2015) In situ forming hydrogel for tissue adhesives and biomedical use thereof. U.S. Pat. No. 8,968,716 B2.

Dalsin, J. L., Koepsel, J. T. (2015) Bioadhesive compounds and methods of synthesis and use.

Shafiq, Z., Cui, J., Pastor-Perez, L., Miguel, V. S., Gropeanu, R. A., Serrano, C., del Campo, A. (2012) Bioinspired underwater bonding and debonding on demand. Angew. Chem. Int. Ed., 51, 4332-4335.

Cencer, M., Murley, M., Liu, Y, Lee, B. P. (2015) Effect of nitro-funtionalization on the cross-linking and bioadhestion of biomimetic adhesive moiety. Biomacromolecules, 16, 404-410.

Ding, X., Vegesna, G. K., Meng, H., Winter, A., Lee, B. P. (2015) Nitro-group functionalization of dopamine and its contribution to the viscoelastic properties of catechol-containing nanocomposite hydrogels. Macromol. Chem. Phys., 216(10), 1109-1119.

Doner, W. (1997) Rapid purification of commercial gellan gum to highly soluble and gellable monovalent cation salts. Carbohydrate Polymers, 32, 245-247.

Gong, Y., Wang, C., Lai, R. C., Su, K., Zhang, F., Wang, D. (2009) An improved injectable polysaccharide hydrogel: modified gellan gum for long-term cartilage regeneration in vitro. J. Mater. Chem., 19, 1968-1977.

Hamcerencu, M., Desbrieres, J., Khoukh, A., Popa, M., Reiss, G. (2008) Synthesis and characterization of new unstarurated esters of gellan gum. Carbohydrate Polmers, 71, 92-100.

Hashimoto, W., Nankai, H., Sato, N., Kawai, S., Murata, K. (1999) Characterisation of an α-L-rhamnosidase of *Bacillus* sp. GL1 responsible for the complete depolymerisation of gellan. Archives of Biochemistry and Biophysics, 368(1), 56-60.

Rodenstein, M., Zurcher, S., Tosaitti, S. G. P., Spencer, N. D. (2010) Fabricating chemical gradients on oxide surfaces by means of fluorinated, catechol-based, self-assembled monolayers. Langmuir, 26(21), 16211-16220.

McCarthy, J. R., McCowan, J., Zimmerman, M. B., Wenger, M. A., Emmert, L. W. (1986) Synthesis and renal vasodilator activity of 2-chlorodopamine and N-substituted derivatives. J. Med. Chem., 29, 1586-1590.

Dobbin, P. S., Hider, R. C., Hall, A. D., Taylor, P. D., Sarpong, P., Porter, J. B., Xiao, G., van der Helm, D. (1993) Synthesis, physicochemical properties and biological evaluation of N-substituted 2-alkyl-3-hydroxy-4 (1H)-pyridinones: orally active iron chelators with clinical potential. J. Med. Chem., 36, 2448-2458.

The invention claimed is:

1. A gellan gum comprising a compound having the structure of Formula I

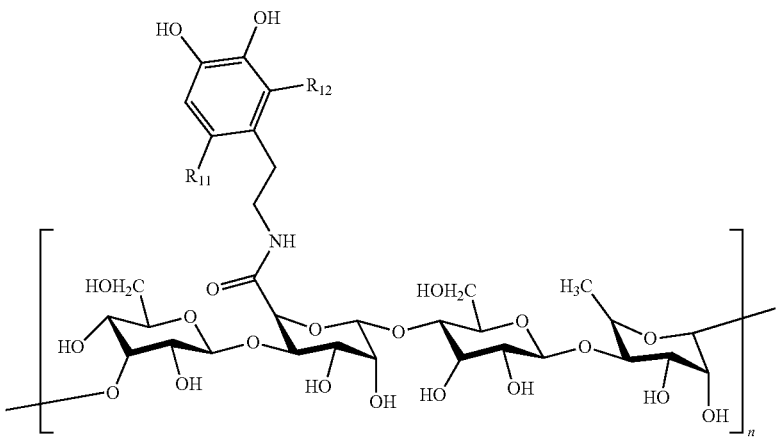

Formula II wherein; $R_{11}$ and $R_{12}$ are independently selected from each other, $R_{11}$ or $R_{12}$ is hydrogen, nitro, cyano or halogen, and n is an integer from 1 to 4000.

2. The gellan gum of claim 1, wherein $R_{11}$ and $R_{12}$ are hydrogen and wherein n is an integer from 50 to 4000.

3. The gellan gum of claim 2, wherein n is an integer from 500 to 4000.

4. The gellan gum of claim 1, wherein the halogen group is selected from the group consisting of: fluorine, chlorine, bromine and iodine.

5. The gellan gum of claim 1, wherein said gellan gum is ionically crosslinkable by one or more monovalent, divalent or trivalent cations, or mixtures thereof, selected from the group consisting of: Na+, K+, Li+, Ca2+, Mg2+, Fe2+, Cu2+, Sr2+, Ba2+, Co2+, Mn2+, Ni2+, Sn2+, Zn2+, Fe3+, Al3+, Ga3+ and Ti3+.

6. The gellan gum of claim 1, wherein the degree of substitution of the gellan gum is between 0.1 and 30%.

7. The gellan gum of claim 1, wherein the gellan gum has a molecular weight from 100 to 2500 KDa.

8. The gellan gum of claim 1, wherein the gellan gum is in the form of a hydrogel, porous scaffold, fibres three-dimensional structure, microparticle, nanoparticle, capsule, membrane, net, gauze, disk or sprayable gel.

9. The gellan gum of claim 1, wherein the gellan gum is a medicament for a human or a non-human subject.

10. The gellan gum of claim 1, wherein the gellan gum is a treatment or therapy for bone, cartilage or soft tissue diseases or lesions.

11. The gellan gum of claim 1, wherein the gellan gum is a treatment or therapy for hyaline cartilage damage.

12. The gellan gum of claim 1, wherein the gellan gum is a treatment or therapy of a disease that is positively influenced by the chondrogenic and/or osteogenic and/or adipogenic differentiation of human mesenchymal stem cells.

13. The gellan gum pf of claim 1, wherein the gellan gum is a treatment or therapy for bone fracture, bone repair or in the treatment of osteopathies or in the treatment of osteochondritis.

14. A hydrogel comprising the gellan gum of claim 1 and a suitable solvent.

15. The hydrogel of claim 14, wherein the suitable solvent is water, a cell culture media, an aqueous saline solvent, or mixtures thereof.

16. The hydrogel of claim 14, wherein the concentration of the gellan gum is between 0.01% and 5% w/V.

17. The hydrogel of claim 14, wherein the concentration of the gellan gum is between 0.5%-2.5% w/V.

18. A composition comprising the gellan gum of claim 1, and a bioactive ingredient selected from the group consisting of a cell, a stem cell, a protein, a biomolecule, a small molecule active substance, a therapeutic agent, a diagnostic marker, and mixtures thereof.

19. The composition of claim 18, wherein the cell or stem cell are selected from a group consisting of: mammalian chondrocytes, mammalian mesenchymal stromal/stem cells, mammalian bone marrow mesenchymal stem cells, and mixtures thereof.

20. The composition of claim 18, further comprising mammalian cells and a physiological ionic solution comprising cations in an effective amount for ionic crosslinking.

21. A composition comprising:
    the gellan gum of claim 1; and
    bone marrow aspirate concentrate, growth factors, antibiotics, or mixtures thereof.

22. A composition comprising:
    a matrix containing the gellan gum of claim 1 or the hydrogel of claim 14; and
    human adipose mesenchymal stromal/stem cells.

23. The composition of claim 18, wherein the cell is an autologous cell encapsulated within the gellan gum.

24. The composition of claim 18, wherein the therapeutic agent is selected from the group consisting of: α-adrenergic agonists; β-adrenergic agonists; α-adrenergic blockers; β-adrenergic blockers; alcohol deterrents; aldose reductase inhibitors; aldosterone antagonists; amino acids; anabolics; analgesics; anesthetics; anorexics, antacids; anthelmimetics; anti-acne agents; anti-allergics; anti-androgens; anti-anginal agents; anti-anxiety agents; anti-arrythmics; anti-asthmatics; antibacterial agents and antibiotics; anti-alopecia and anti-baldness agents; anti-amebics; antibodies; anticholinergic drugs; anticoagulants and blood thinners; anticolitis drugs; anticonvulsants and anti-epileptic drugs; anticystitis drugs; antidepressants; antidiabetic agents; antidiarrheal agents; antidiruetics; antidotes; anti-emetics; anti-estrogens; anti-flatulents; antifungal agents; antigens; antiglaucoma agents; antihistaminics; antihyperactives; antihyperthyroid agents; antihyperlipoproteinemetics; antihypertensives; antihypotensives; anti-infectives; anti-inflammatory agents; antimalarials; antimigraine agents; antineoplastics; anti-obesity agents; antiparkinsonian agents; antidyskinetics; antipneumonia agents; antiprotozoal agents; antipruritics; antipsoriatics; antipsychotics; antipyretics; antiheumatics; antisecretory agents; antishock medications; antispasmodics; antithrombotics; antitumour agents; antitussives; anti-ulceratives; antiviral agents; anxiolytics; bactericidins; bone densifiers; bronchodilators; calcium channel blockers; carbonic anhydrase inhibitors; cardiotonics and heart stimulants; chemotherapeutics; choloretics; cholinergics; chronic fatigue syndrome medications; CNS stimulants and depressants; coagulants; contraceptives; cystic fibrosis medications; decongestants; diuretics; dopamine receptor agonists and antagonists; enzymes, estrogens; expectorants; gastric hyperactivity medications; glucocorticoids; hemostatics; HMG CoA reductase inhibitors; hormones; hypnotics; immunomodulators; immunosuppressants; laxatives; medicaments for oral and periodontal diseases; miotics; monoamine oxidase inhibitors; mucolytics; multiple sclerosis medications; muscle relaxants; mydriatics; narcotic antagonists; NMDA receptor antagonists; oligonucleotides; ophthalmic drugs, oxytocics; peptides, polypeptides; proteins; polysaccharides; progestogens; prostaglandins; protease inhibitors; respiratory stimulants; sedatives; serotonin uptake inhibitors; sex hormones; smoking cessation drugs; smooth muscle relaxants and stimulants; steroids; thrombolytics; tranquilizers; urinary acidifiers; urinary incontinence medications; vasodilators; vasoprotectants; skin protectants and sunscreens, or mixtures thereof.

25. The composition of claim 21, wherein the growth factor is TGF-β1, bone morphogenetic protein-2 (BMP-2), BMP-7 (osteogenic protein-1 [OP-1]) or cartilage-derived morphogenetic proteins CDMP-1 and CDMP-2, platelet lysates, or mixtures thereof.

26. The composition of claim 18, wherein the composition is in an injectable formulation.

27. A mesh, disk, scaffold, three-dimensional structure, strip, net, gause or membrane comprising the gellan gum of claim 1 or the hydrogel of claim 14, or the composition of claim 18.

28. A transdermal therapeutic patch comprising the gellan gum of claim 1, or the hydrogel of claim 14, or the composition of claim 18.

29. A kit for use in use in tissue engineering, regenerative medicine, or in vitro cell culture comprising a matrix containing the gellan gum of claim 1, or the hydrogel of claim 14, or the composition of claim 18, and mammalian cells.

30. A process for obtaining the gellan gum of claim 1, comprising: reacting a gellan gum according to Formula II $M^+$ is a monovalent alkali metal ion chosen from the group $Na^+$, $K^+$ and $Li^+$; or a group $NX_4$ wherein X is hydrogen or a C1-C4 alkyl group chosen from methyl, ethyl, propyl or butyl, wherein the gellan gum of Formula II is reacted with, a primary amine or a secondary amine having the formula HN—$R_7R_8$, wherein $R_7$, $R_8$ are independently selected from each other and wherein $R_8$ is hydrogen or a $C_1$-$C_6$ alkyl group, and wherein $R_7$ represents a group according to the following formula: -$(CH_2)_g$-B wherein g is an integer from 0 to 18, B is a phenol or catechol group optionally substituted on the aromatic ring by one or more, or combinations of the following groups:

$C_1$-$C_6$ alkyl groups, hydroxyl, nitro, cyano, trifluoromethyl or halogen groups;

lower alkoxy groups —$OR_1$ wherein $R_1$ represents a $C_1$-$C_6$ alkyl group; a —$C(O)$-$R_2$ group, wherein $R_2$ represents hydrogen or a $C_1$-$C_6$ alkyl group; a —$C(O)$—$OR_3$ group, wherein $R_3$ represents hydrogen or a $C_1$-$C_6$ alkyl group; a —$C(O)NR_4R_5$ group, wherein $R_4$ and $R_5$ represent hydrogen or $C_1$-$C_6$ alkyl groups; or a —$SO_2R_6$ group, wherein $R_6$ represents hydrogen or a $C_1$-$C_6$ alkyl group, or B is a 3-hydroxy-4-pyridinone or a 5-hydroxypyrimidone-4 (3H)-one group, and wherein the gellan gum of Formula II is reacted in the presence of at least one coupling agent and optionally in the presence of a non-nucleophilic base.

* * * * *

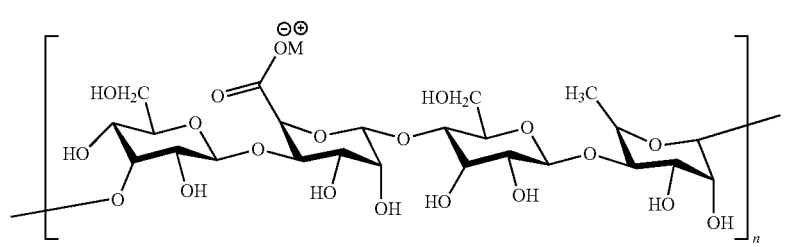

Formula II wherein n is an integer from 1-4000,